US005312427A

United States Patent [19]

Shturman

[11] Patent Number: 5,312,427
[45] Date of Patent: May 17, 1994

[54] DEVICE AND METHOD FOR DIRECTIONAL ROTATIONAL ATHERECTOMY

[75] Inventor: Leonid Shturman, Minneapolis, Minn.

[73] Assignee: Shturman Cardiology Systems, Inc., Minnetonka, Minn.

[21] Appl. No.: 962,634

[22] Filed: Oct. 16, 1992

[51] Int. Cl.⁵ .............................................. A61B 17/32
[52] U.S. Cl. .................................. 606/159; 606/170; 606/180
[58] Field of Search .............. 606/159, 170, 171, 180; 604/22, 96; 128/750-755

[56] References Cited

U.S. PATENT DOCUMENTS

| Re. 33,569 | 4/1991 | Gifford, III et al. |
|---|---|---|
| Re. 33,911 | 5/1992 | Samson et al. |
| 4,445,509 | 5/1984 | Auth |
| 4,679,557 | 7/1987 | Opie et al. |
| 4,781,186 | 11/1988 | Simpson et al. |
| 4,794,931 | 1/1989 | Yock |
| 4,887,606 | 12/1989 | Yock et al. |
| 4,917,097 | 4/1990 | Proudian et al. |
| 4,917,103 | 4/1990 | Gambale et al. |
| 4,926,858 | 5/1990 | Gifford, III et al. |
| 4,950,277 | 8/1990 | Farr |
| 4,979,951 | 12/1990 | Simpson |
| 4,984,581 | 1/1991 | Stice |
| 4,990,134 | 2/1991 | Auth |
| 5,000,185 | 3/1991 | Yock |
| 5,007,434 | 4/1991 | Doyle et al. |
| 5,010,886 | 4/1991 | Passafaro et al. |
| 5,024,234 | 6/1991 | Leary et al. |
| 5,029,588 | 7/1991 | Yock et al. |
| 5,047,040 | 9/1991 | Simpson et al. |
| 5,053,044 | 10/1991 | Mueller et al. |
| 5,054,492 | 10/1991 | Scribner et al. |
| 5,067,489 | 11/1991 | Lind |
| 5,071,424 | 12/1991 | Reger |
| 5,074,871 | 12/1991 | Groshong |
| 5,092,873 | 3/1992 | Simpson et al. |
| 5,100,424 | 3/1992 | Jang et al. |
| 5,115,814 | 5/1992 | Griffith et al. ............... 128/660.03 |

FOREIGN PATENT DOCUMENTS

| 0359447 | 3/1990 | European Pat. Off. |
| 9004657 | 8/1990 | PCT Int'l Appl. |
| 9101813 | 3/1991 | PCT Int'l Appl. |
| 9105844 | 8/1991 | PCT Int'l Appl. |

OTHER PUBLICATIONS

"Rotablator ®, a Revolution in Agioplasty," Heart Technology Inc., Bellevue, Wash., 98005 USA.
McCarty, Lyle H., "Catheter Clears Coronary Arteries," *Design News*, Sep. 23, 1991, pp. 88–92.

(List continued on next page.)

Primary Examiner—Stephen C. Pellegrino
Assistant Examiner—William Lewis
Attorney, Agent, or Firm—Gregory P. Kaihoi

[57] ABSTRACT

Device and method for performing an atherectomy. The device utilizes a dual lumen catheter, with a guide wire being receivable in one of these lumens, and a flexible, elongated drive shaft carrying an abrasive burr at its distal end being disposed in the other lumen. The drive shaft and abrasive burr each include a central lumen so that they can be advanced over a positioning wire. The positioning wire has a generally straight proximal portion, and a distal end that is slidably secured to the guide wire so that the positioning wire can be moved proximally and distally with respect to the guide wire. The positioning wire also includes a distal end portion with a burr positioning segment. The burr positioning segment has a predetermined curved shape so that when the abrasive burr is advanced over the positioning wire to a position along the curved burr positioning segment, the burr positioning segment positions the burr laterally away from the guide wire, thus giving control over the lateral position of the burr within an artery. The device therefore allows selective removal of tissue from one side of an artery, permitting selective treatment of eccentric stenotic lesions without damaging the artery wall, and permitting treatment of lesions generally without blocking blood flow through the artery during use of the device.

32 Claims, 19 Drawing Sheets

OTHER PUBLICATIONS

"Premier Presents Two Striper® Dental Diamond Instruments," Abrasive Technology Inc., Westerville, Ohio USA.

Gilmore, H. W., et al., "Instrumentation," *Operative Dentistry*, 4th Ed., Ch. 4, pp. 55, 64–73, The C. V. Mosby Company, 1982.

Gilmore, H. W., et al., *Operative Dentistry*, 4th Ed., pp. 348–351, 353–354, The C. V. Mosby Company, 1982.

"Premier Two Striper® Gingival Curettage," Abrasive Technology Inc., Westerville, Ohio USA.

"Premier Two Striper® Crown & Bridge Techniques," Abrasive Technology, Inc., Westerville, Ohio USA.

Tupac, Robert G., et al, "A Comparison of Cord Gingival Displacement with the Gingitage Technique," *The Journal of Prosthetic Dentistry*, Nov. 1981, vol. 46, No. 5, pp. 509–515.

*Atherectomy, A Physician's Guide*, Strategic Business Development, Inc., Kauai, Hi. 96714 USA, 1990, pp. 1–114.

Bom, N., et al, "Early and Recent Intraluminal Ultrasound Devices," *International Journal of Cardiac Imaging*, 4:79–88, 1989.

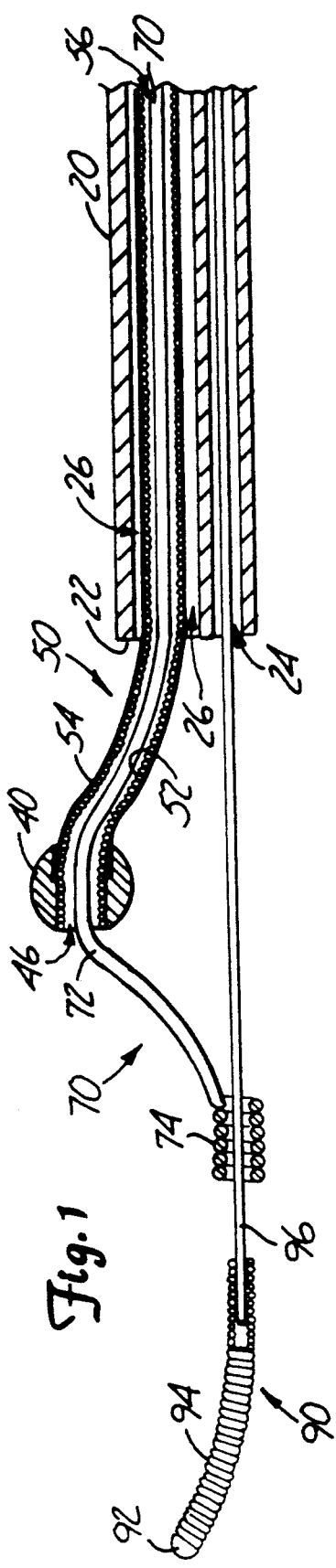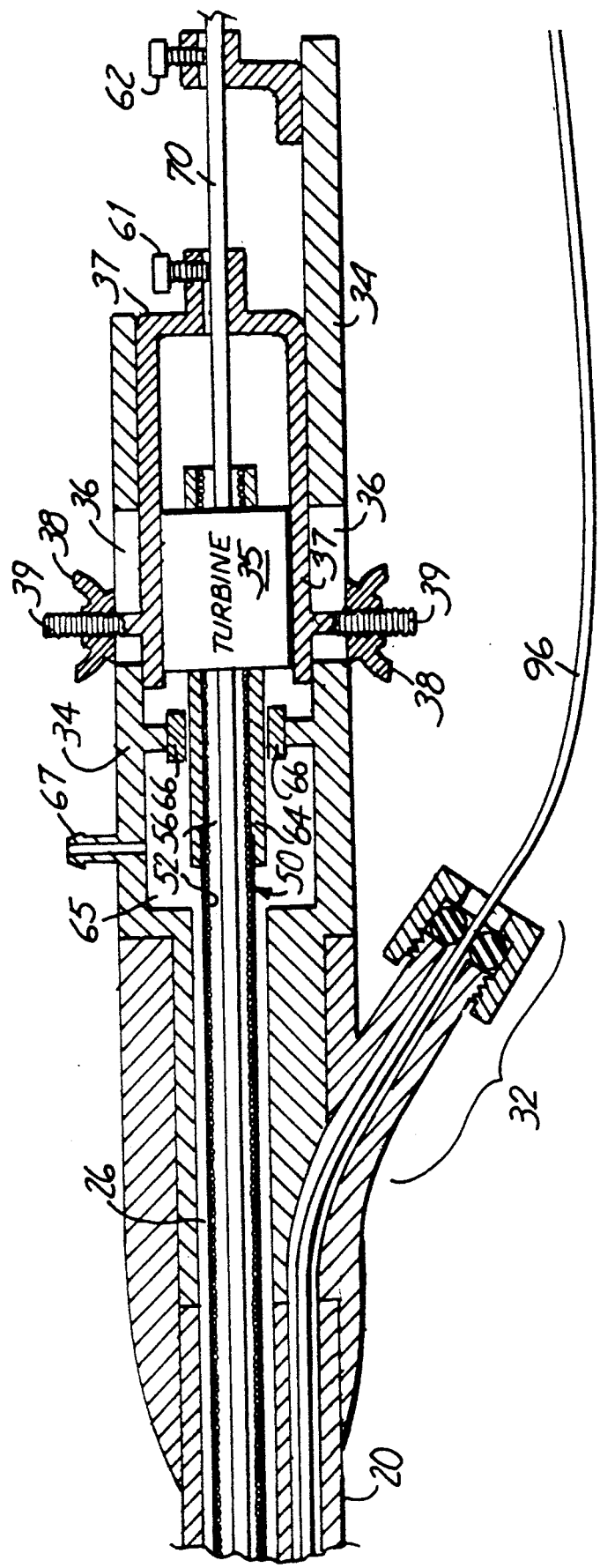
Fig. 1

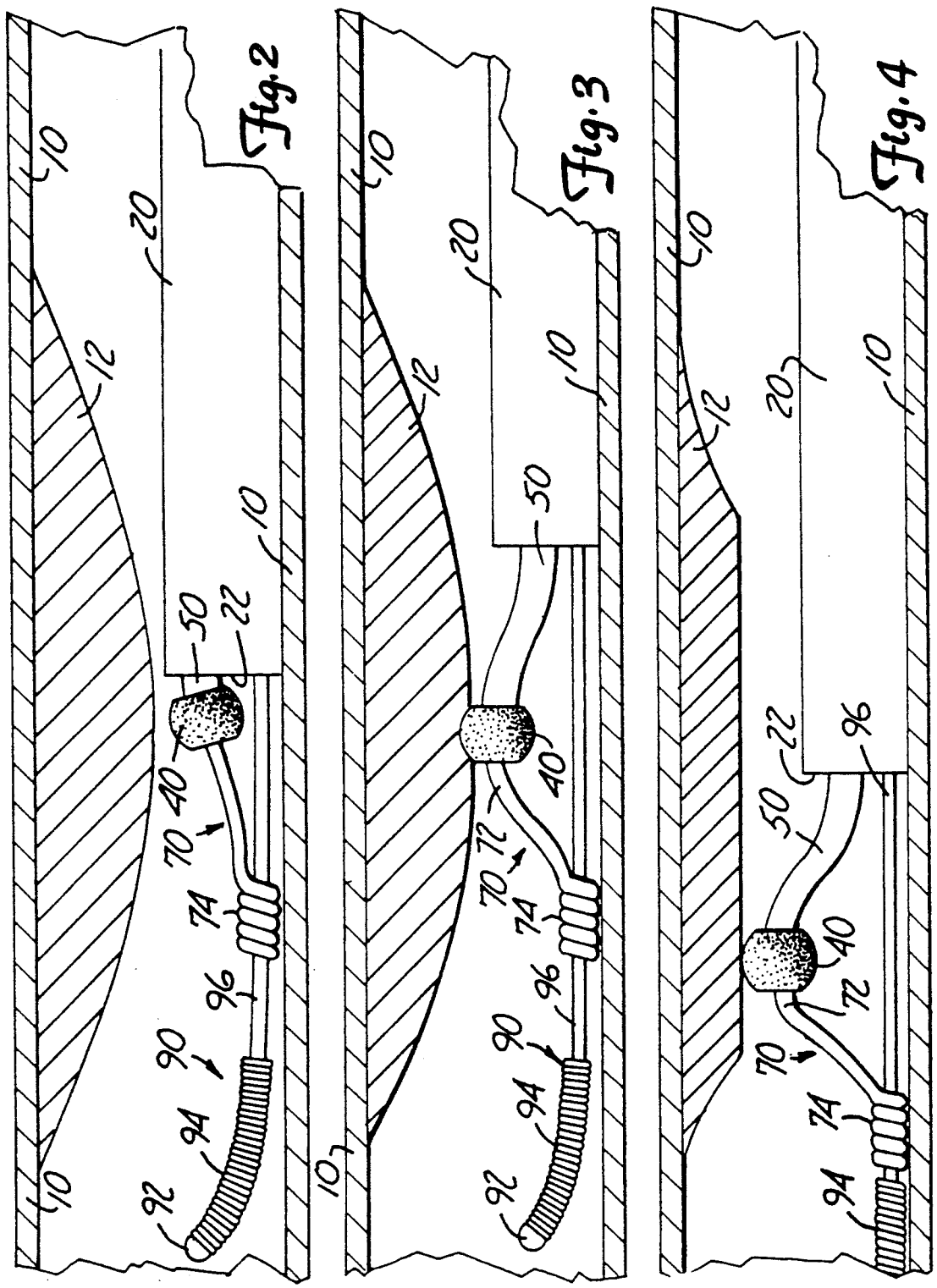

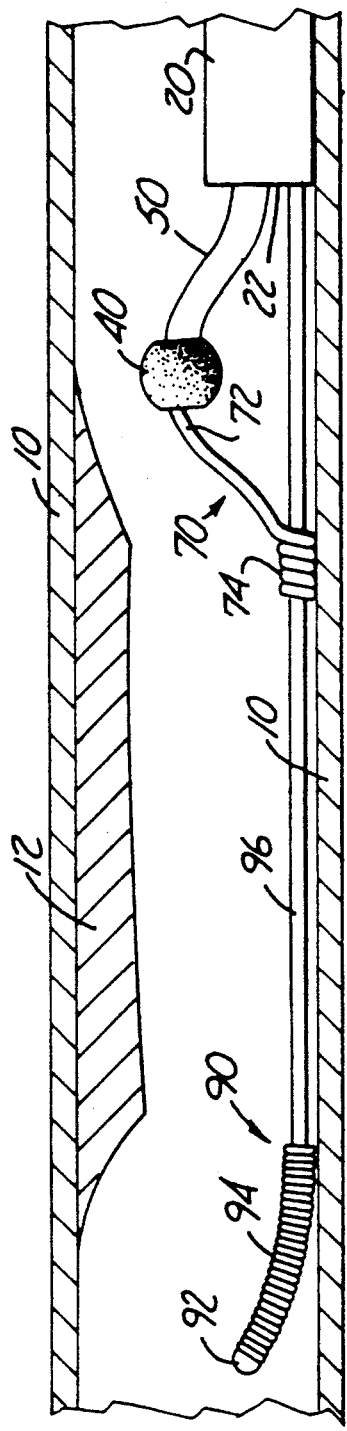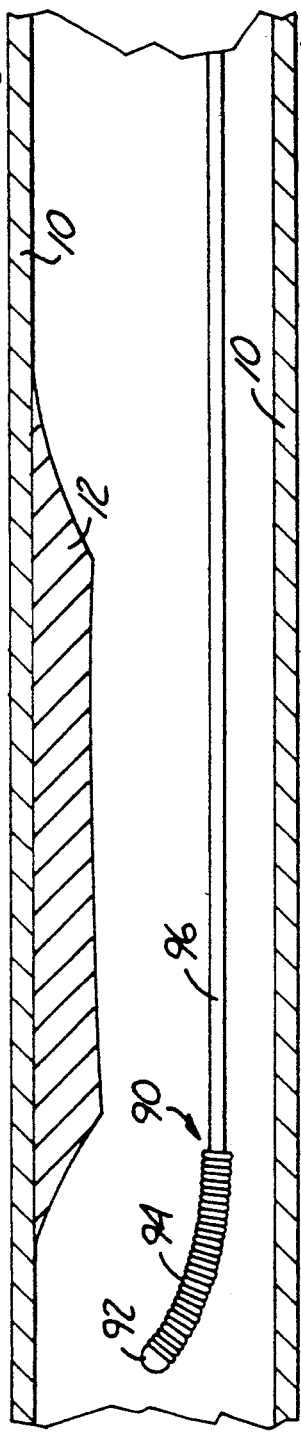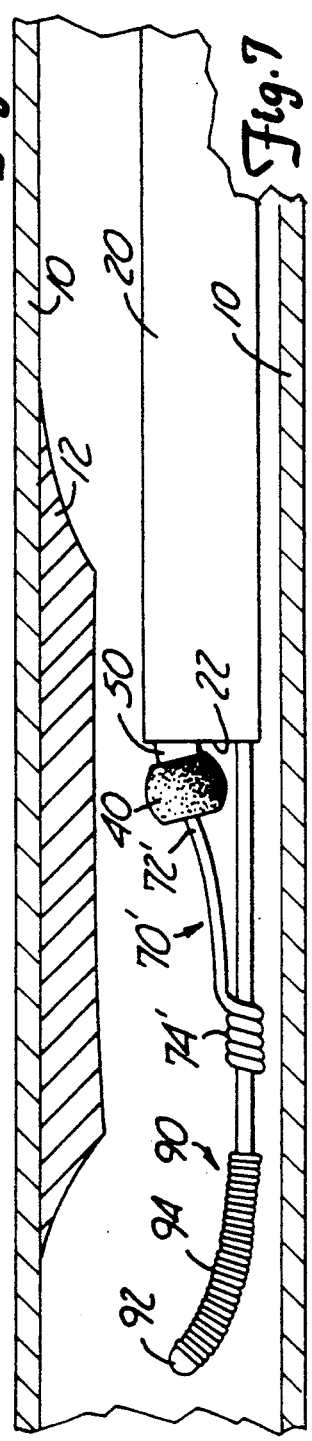

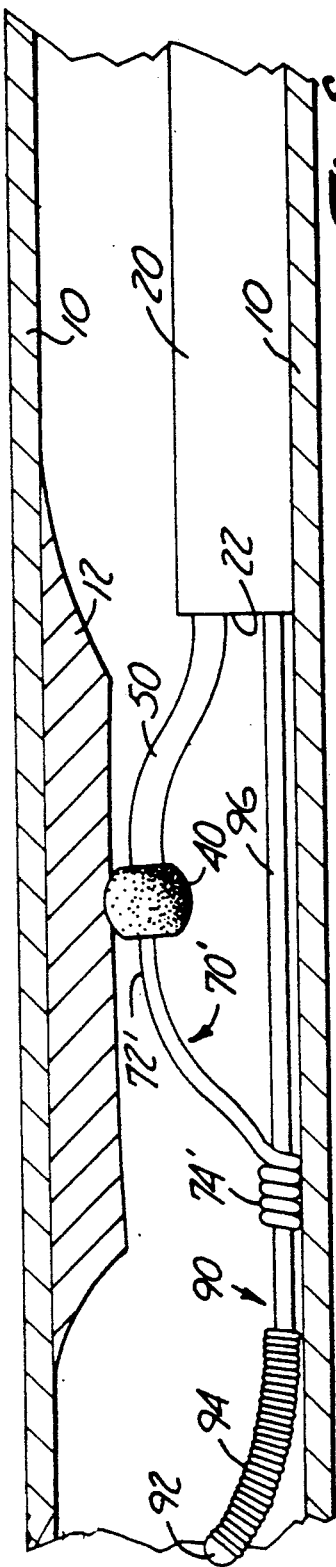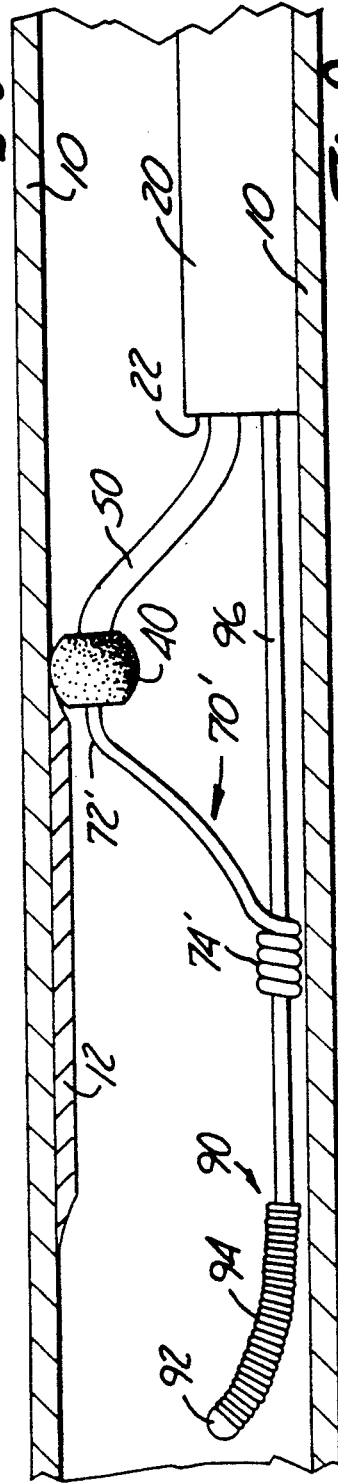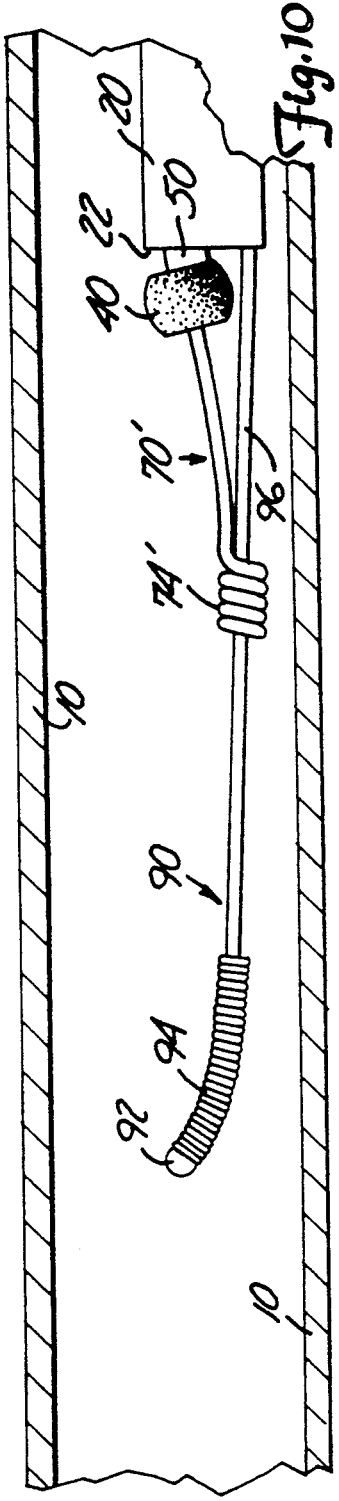

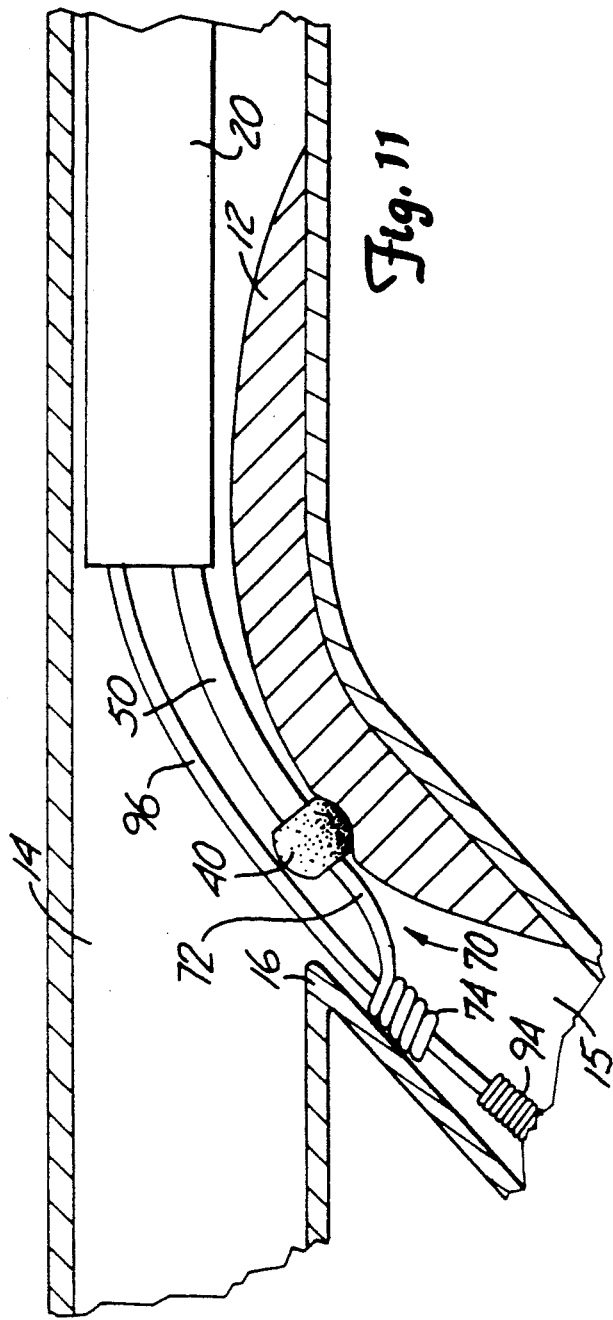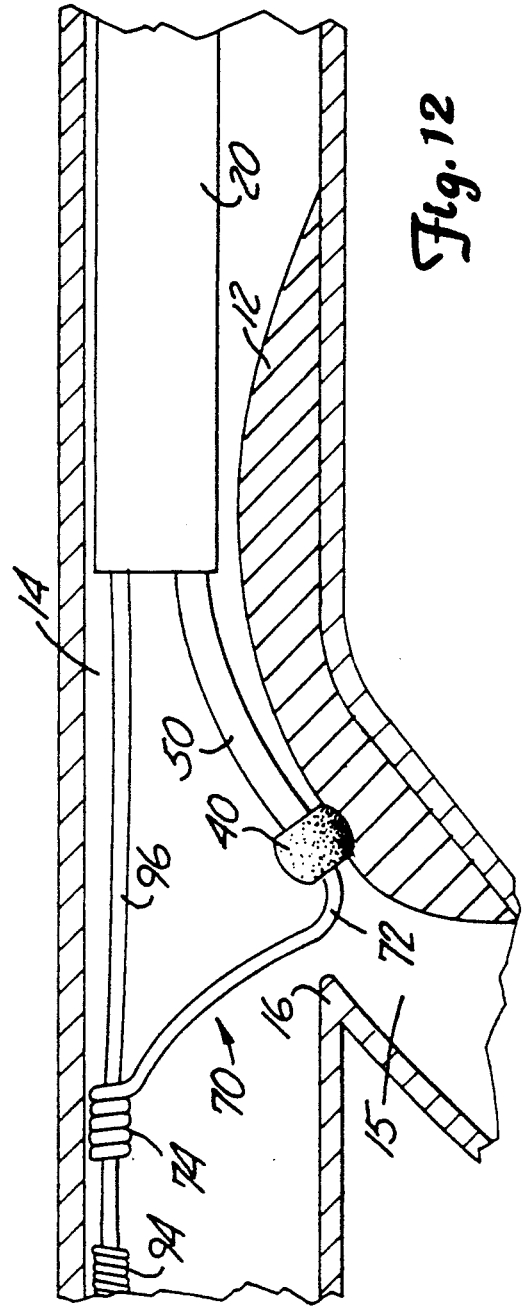

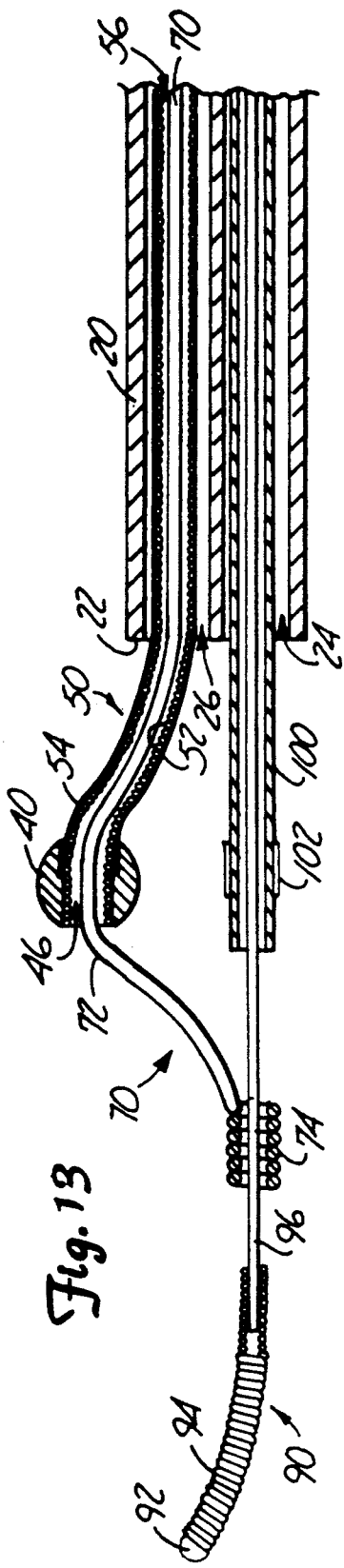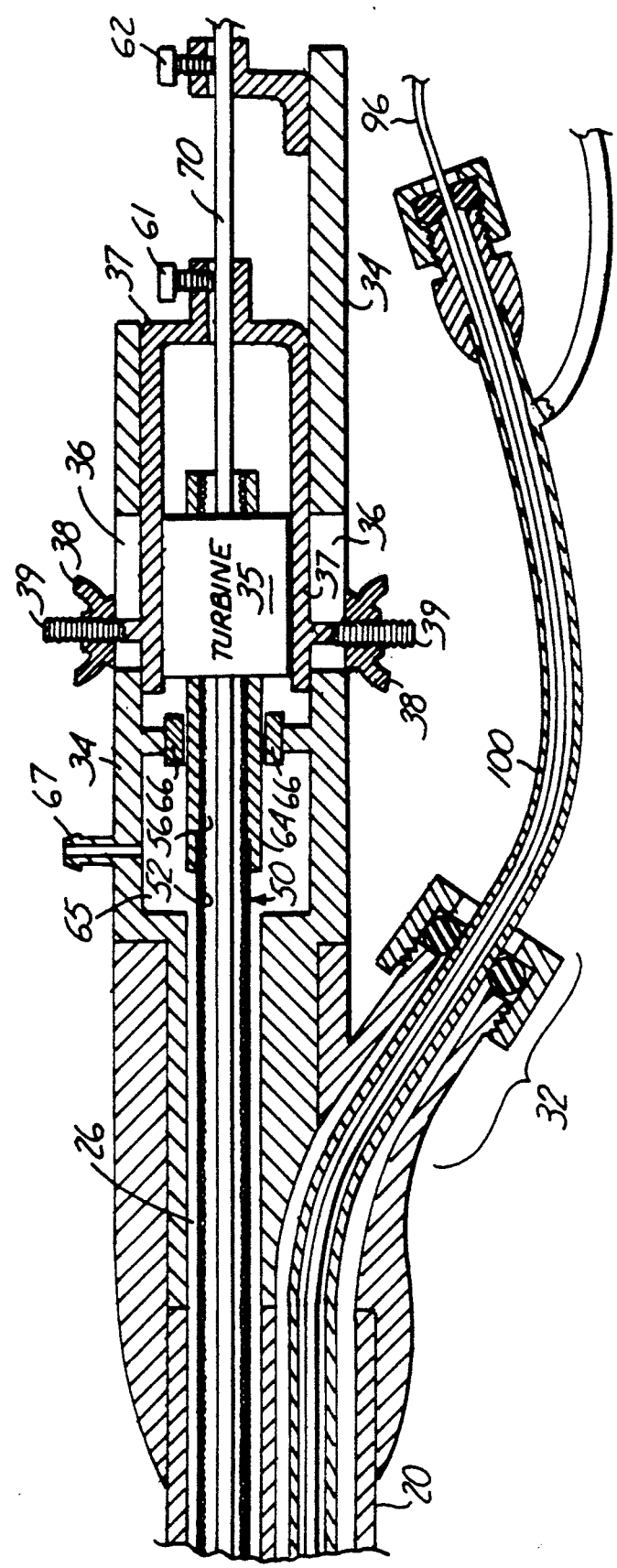

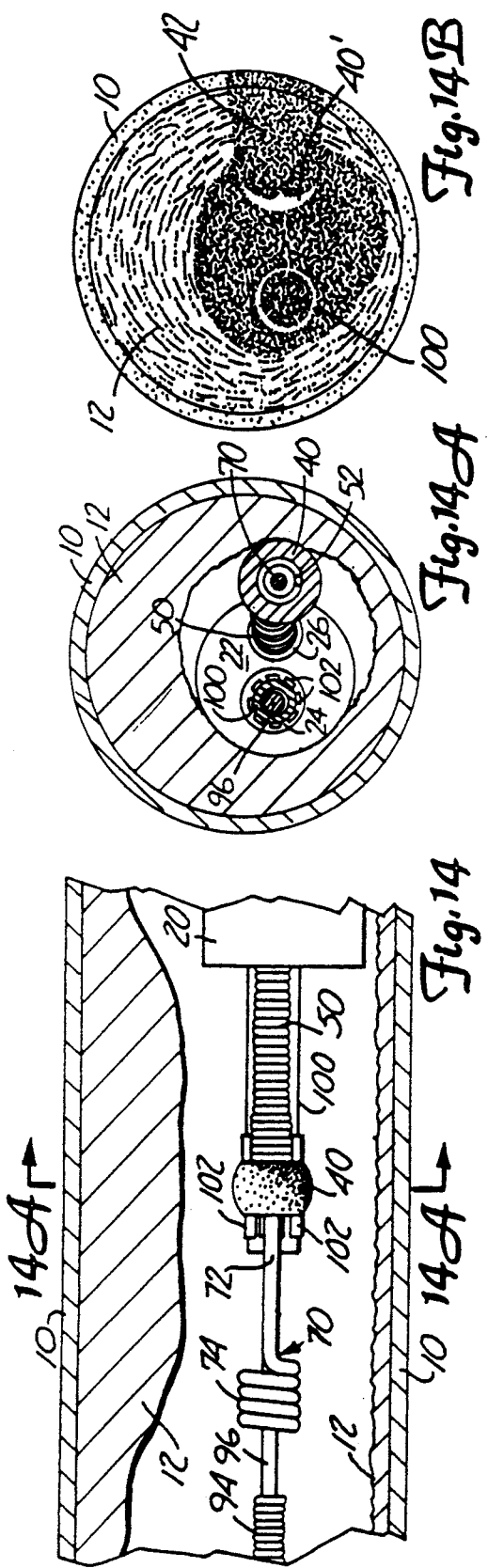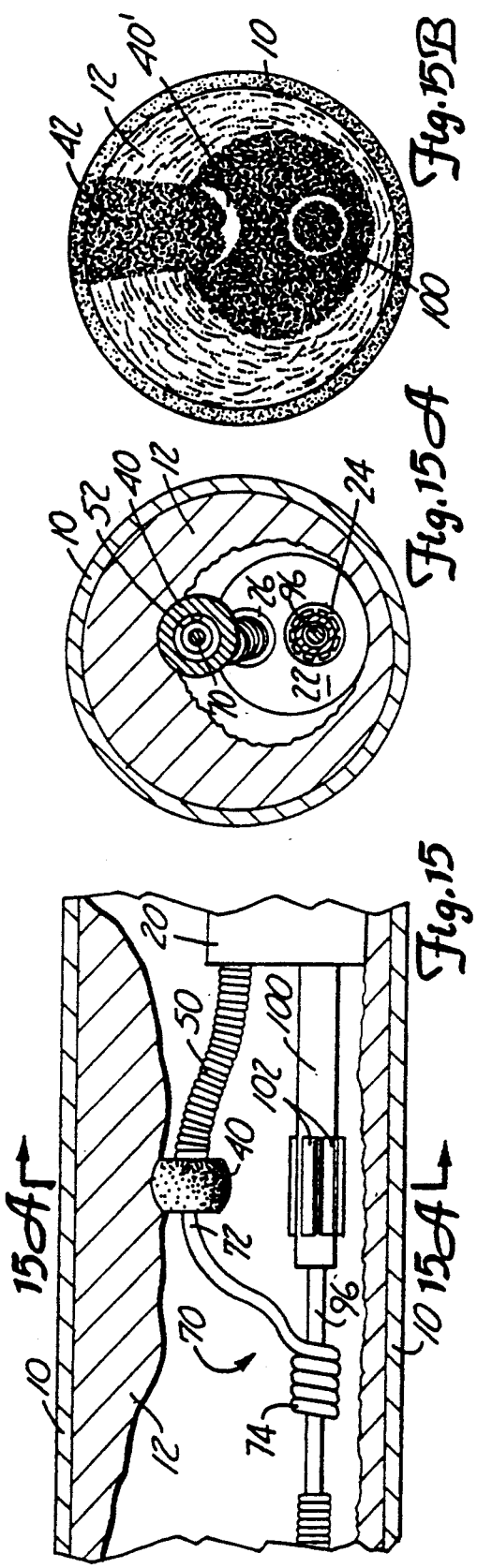

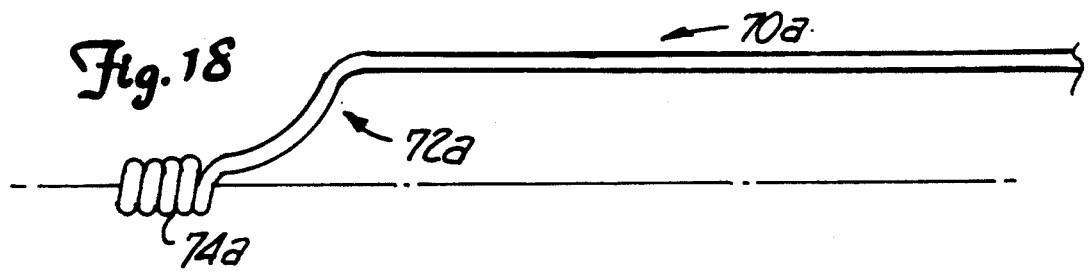
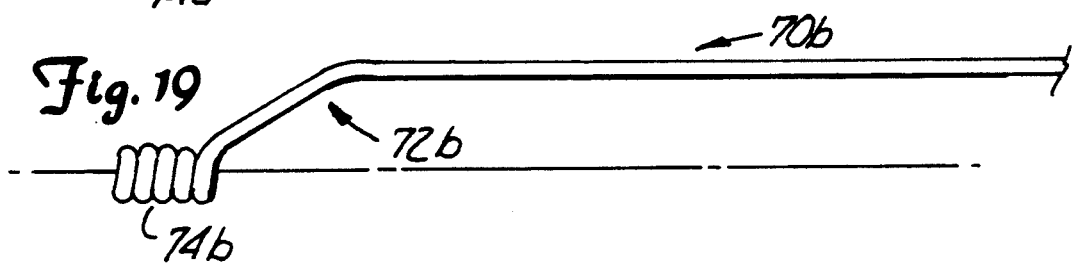
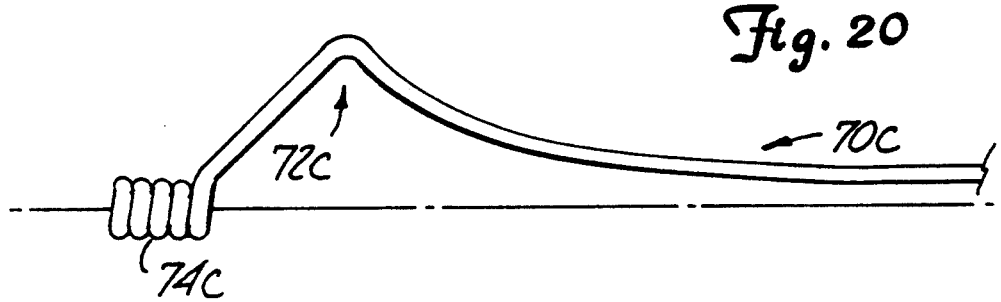
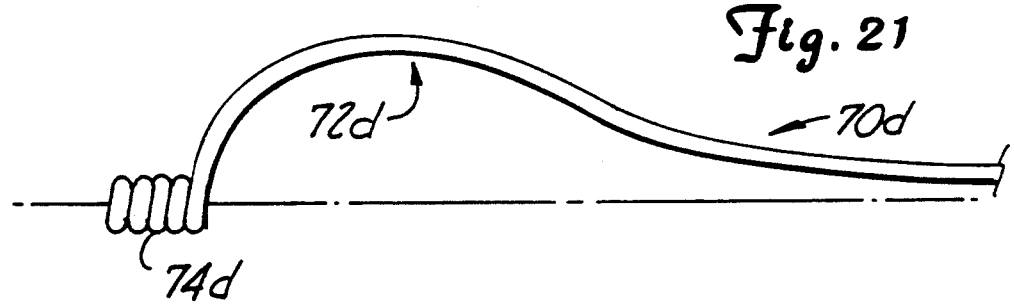
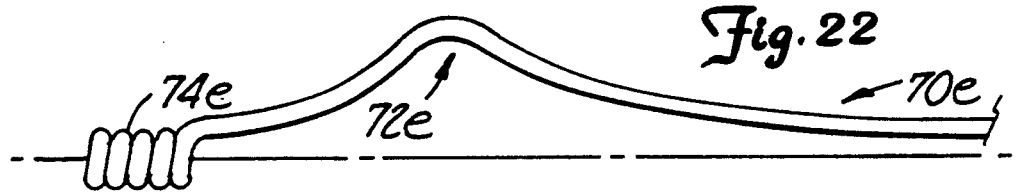

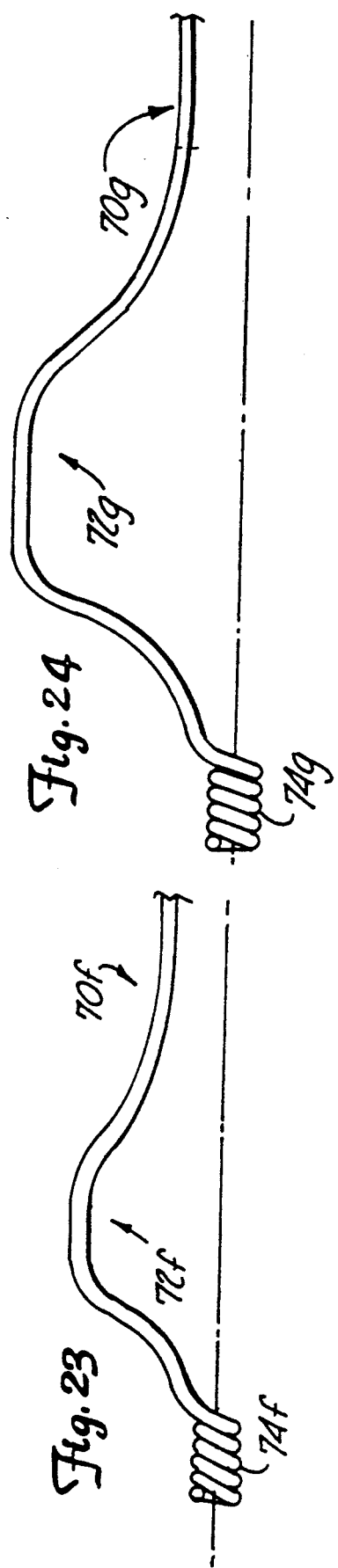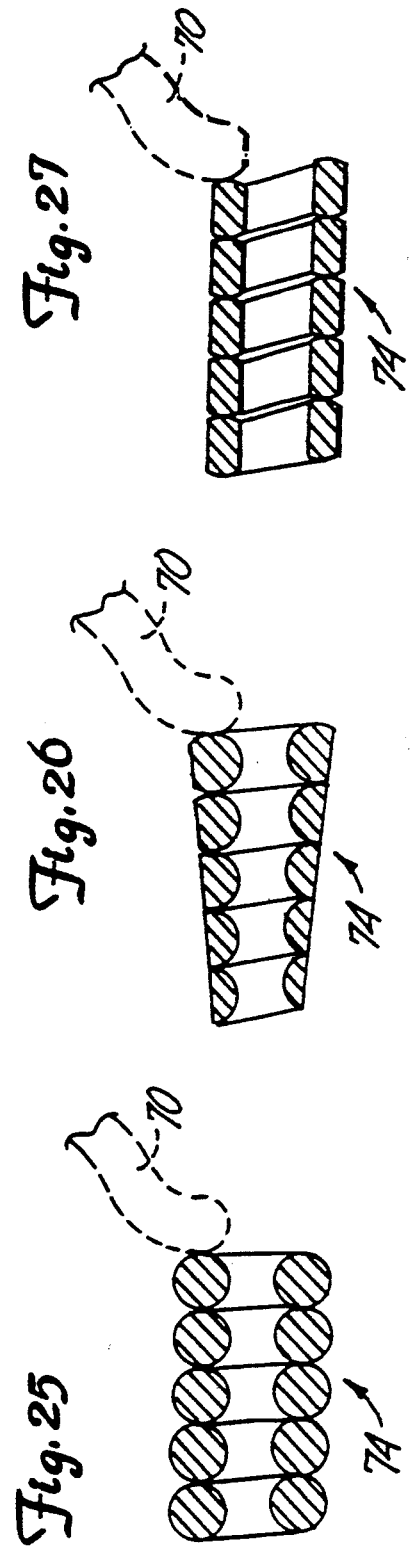

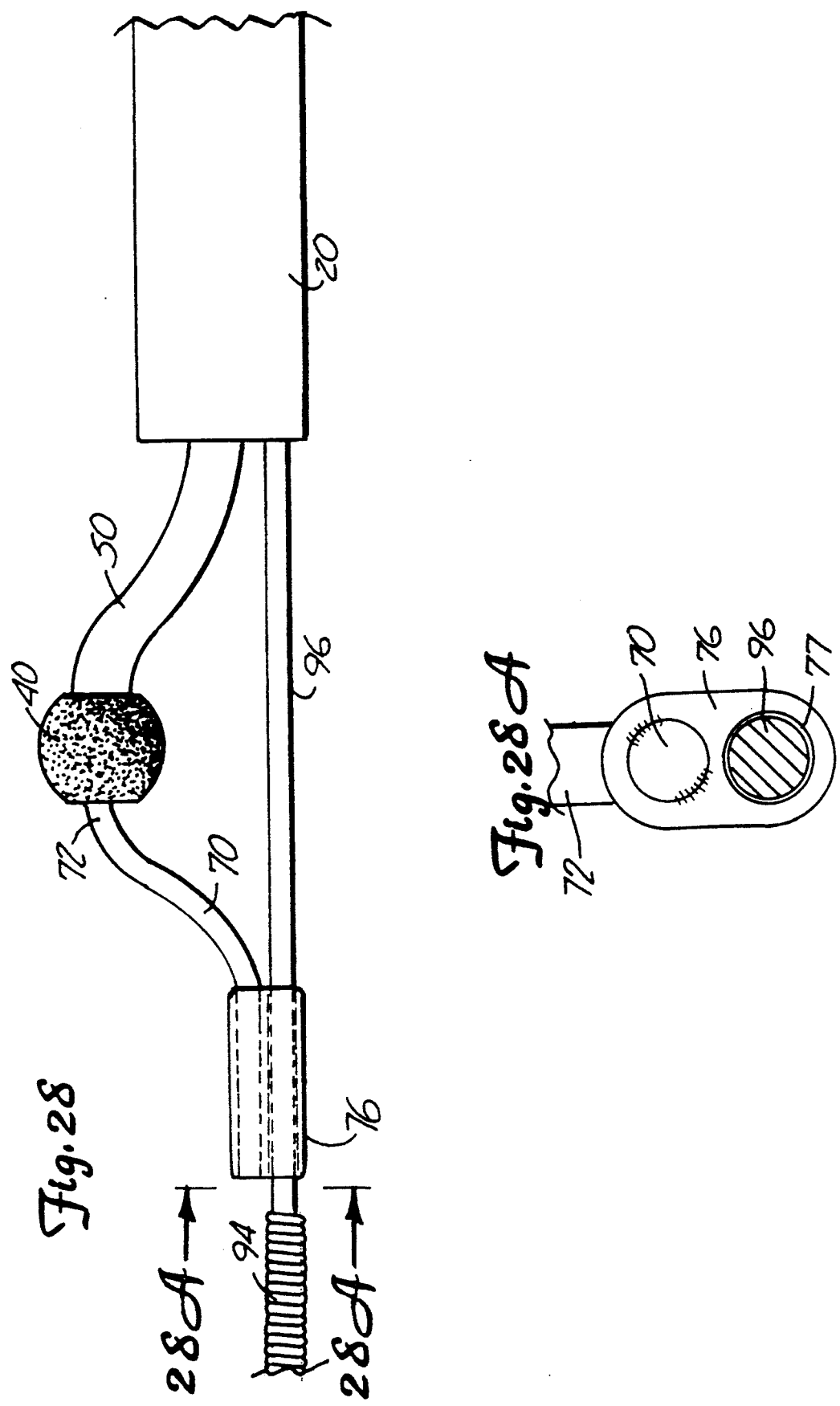

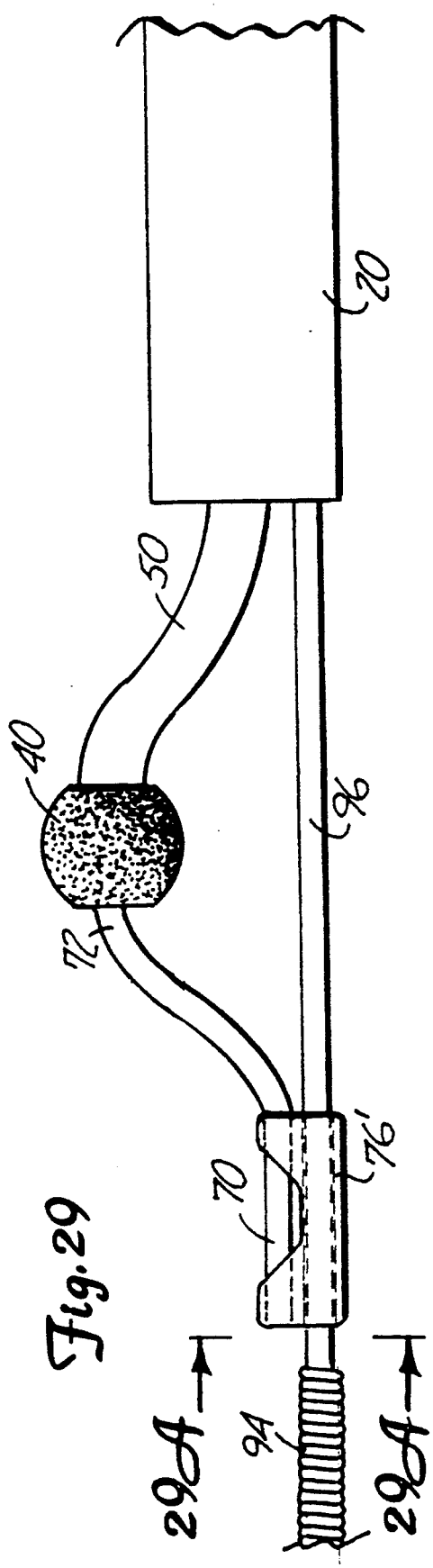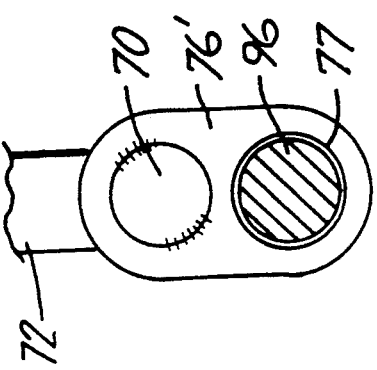

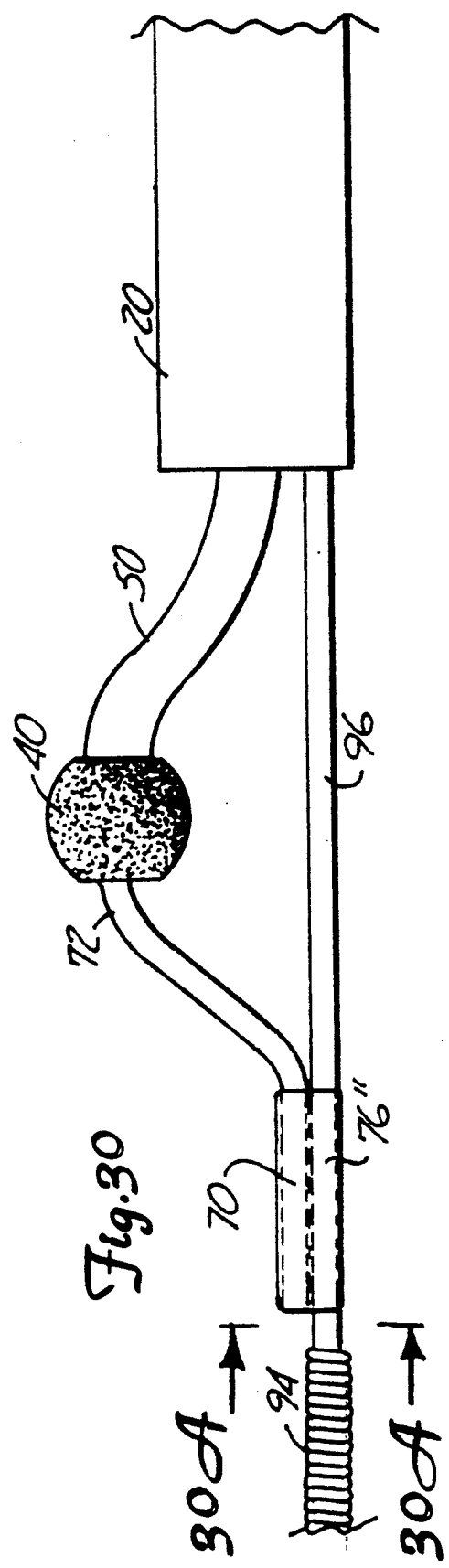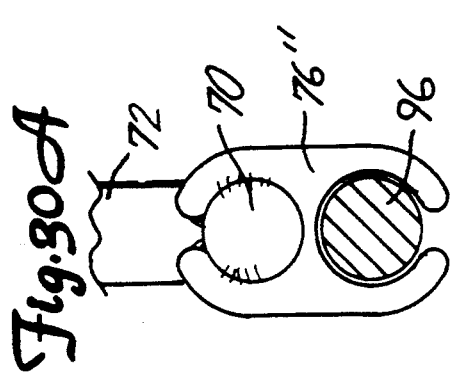

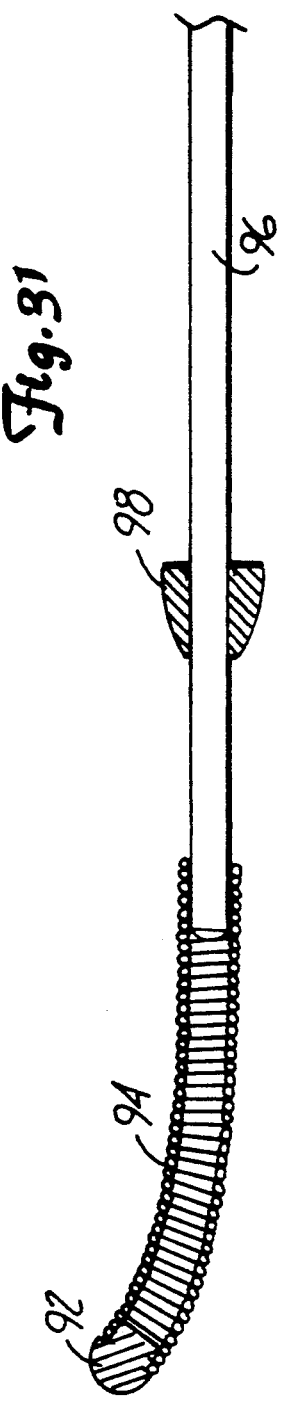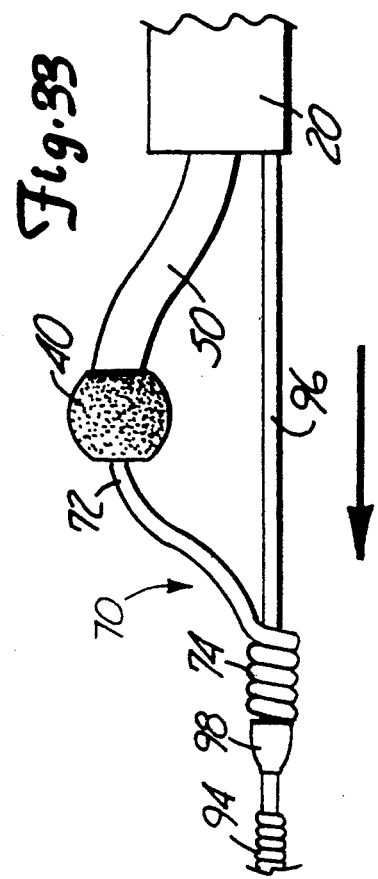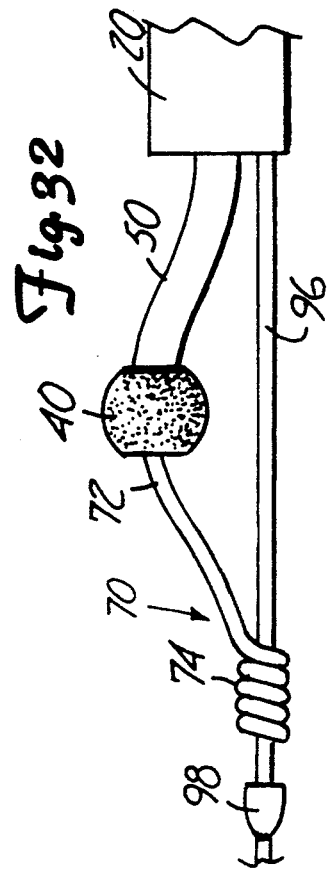

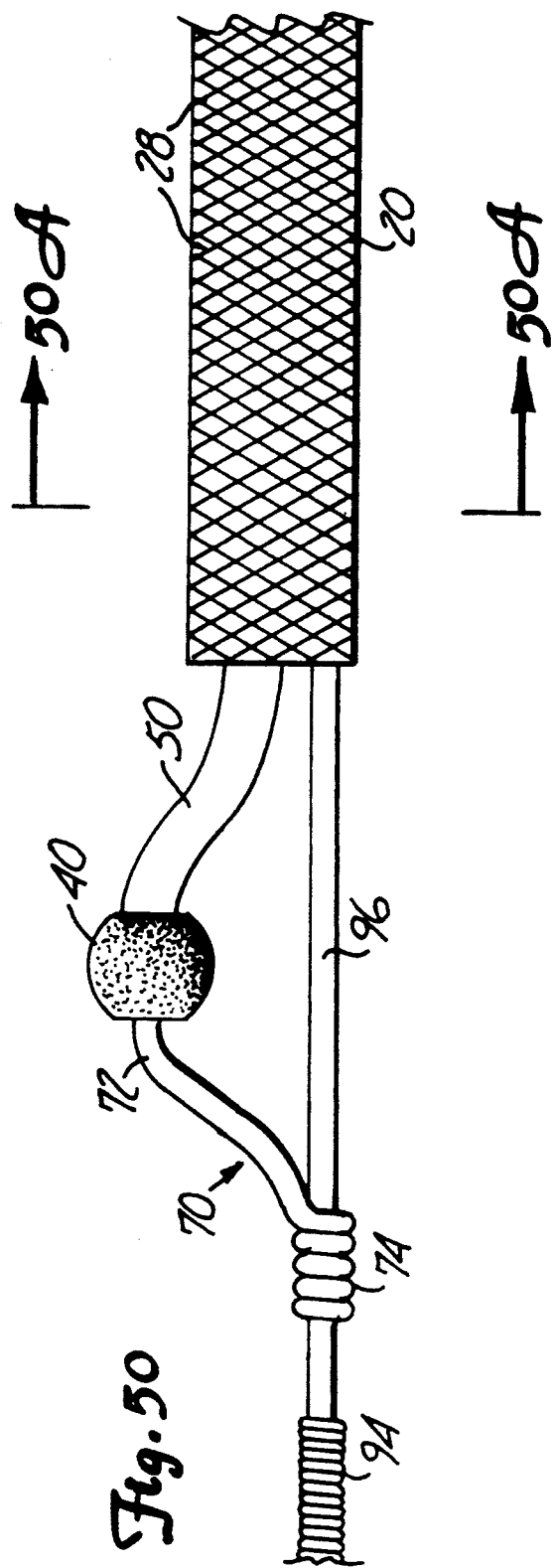
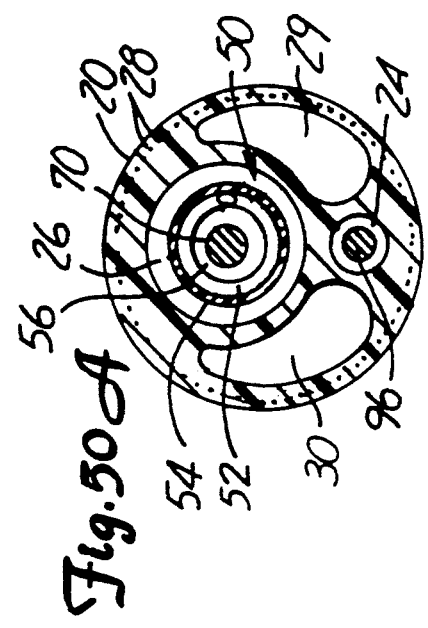
Fig. 50
Fig. 50A

DEVICE AND METHOD FOR DIRECTIONAL ROTATIONAL ATHERECTOMY

FIELD OF THE INVENTION

The invention relates to devices and methods for removing tissue from body passageways, such as removal of atherosclerotic plaque from arteries, utilizing a rotary atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft cholesterol-rich atheromatous material hardens into a calcified atherosclerotic plaque. Such atheromas restrict the flow of blood, and therefore are often referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 5,092,873 (Simpson), a cylindrical housing, canned at the distal end of a catheter, has a portion of its side-wall cut out to form a hollow housing into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device—in turn, the length and relative rigidity of the housing limits the maneuverability and therefore the utility of the device in narrow and tortuous passageways such as coronary arteries.

Another approach which solves some of these problems involves the use of a rotating burr covered with an abrasive cutting material such as diamond grit (diamond particles or dust) carried at the distal end of a flexible drive shaft, similar to a dental abrading/polishing tool. Examples of such devices are illustrated in U.S. Pat. No. 4,990,134, (issued to Auth), as well as "Premier Two Striper® Gingival Curettage" (Abrasive Technology, Inc. 1982); "Premier Two Striper® Crown & Bridge Techniques" (Abrasive Technology, Inc. 1981); H. Gilmore, et. al, operative Dentistry (C. V. Mosby Company 1982, 4th ed.), pp. 64–65, 69, 348–350; R. Tupac, et al., "A Comparison of Cord Gingival Displacement With the Gingitage Technique," *Journal of Prosthetic* (Nov. 1981, pp.509–515); and Premier Presents Two Striper® Dental Diamond Instruments (Abrasive Technology, Inc. 1989). The burr in such devices is rotated at speeds in the range of 20,000 to 200,000 rpm or more, which, depending on the diameter of the burr, can provide surface speeds of the abrasive particles on the burr above or below 40 ft/sec. Auth claims that at surface speeds below 40 ft/sec the abrasive burr will remove hardened atherosclerotic material but will not damage normal elastic soft tissue of the vessel wall. Auth also admits that at surface speeds above 40 ft/sec the abrasive burr will remove both hardened and soft tissue. See, e.g., U.S. Pat. No. 4,990,134 at col. 3, lines 20–23. Unfortunately not all atherosclerotic plaques are hardened, calcified atherosclerotic plaques. Moreover, the mechanical properties of the soft plaques are very often quite close to the mechanical properties of the soft wall of the vessel. Thus, one cannot safely rely entirely on the differential cutting properties of such abrasive burrs to remove atherosclerotic material from an arterial wall, particularly where one is attempting to entirely remove all or almost all of the atherosclerotic material. See, e.g., *Atherectomy, A Physicians Guide,* (Strategic Business Development, Inc., 1990), pp. 89, 94–96. Furthermore, the Auth burr effectively blocks blood flow through the artery during the passage of the burr through the stenosis, thus limiting the amount of time of each pass across the stenosis to less than one minute (and perhaps as little as 10 seconds). See id. at pp. 95–96. Because the size of the particles removed by the Auth burr is very small (typically 5 microns or less), and because of the time limitations described above, in clinical practice, in order to remove a sufficient amount of tissue during each pass of the burr across the stenosis, the Auth burr is virtually always rotated at speeds of at least about 155,000 rpm. At such speeds a diamond dust covered burr with a diameter of 1.5 mm achieves a surface speed of 40 ft/sec, the very speed at which the differential cutting effect becomes limited, at best (i.e., the burr removes both hard and soft tissue).

The ability of diamond dust covered burrs to remove human soft tissue at high surface speeds (e.g., small diameter burrs rotated at about 200,000 rpm) has been known for some time and has been utilized in dentistry since at least the early 1980's to remove soft gum tissue (see, e.g., "Premier Two Striper® Gingival Curettage" (Abrasive Technology, Inc. 1982); "Premier Two Striper® Crown & Bridge Techniques" (Abrasive Technology, Inc. 1981); H. Gilmore, et. al, *Operative Dentistry* (C. V. Mosby Company 1982, 4th ed.), pp. 348–350; R. Tupac, et al., "A Comparison of Cord Gingival Displacement With the Gingitage Technique," *Journal of Prosthetic Dentistry* (Nov. 1981, pp.509–515).

Several problems have been recognized in use of the Auth-type of burr, however. First, although under some conditions the differential cutting properties of such burrs are effective to protect healthy tissue, in many circumstances the burr nevertheless can abrade at least a portion of the healthy tissue, creating a risk of perforation. This is particularly true at higher rotational speeds. A majority of atherosclerotic lesions are asymmetrical (i.e., the atherosclerotic plaque is thicker on one side of the artery than on the other). Moreover, pressure of the burr against the atherosclerotic plaque is achieved only by the use of a burr having a diameter slightly larger than the opening through the stenotic passageway. Thus, since the stenotic material will be entirely removed on the thinner side of an eccentric lesion before it will be removed on the other, thicker side of the lesion, during removal of the remaining thicker portion of the atherosclerotic plaque the burr necessarily will be engaging healthy tissue on the side which has been cleared--indeed, lateral pressure by such healthy tissue against the burr is required to keep the burr in contact with the remaining stenotic tissue on the opposite side of the passageway. For stenotic lesions that are entirely on one side of an artery (a relatively frequent condition), this means that the healthy tissue across from the stenotic lesion will be exposed to and in contact with the abrasive burr for substantially the entire procedure. Moreover, pressure from that healthy tissue against the burr will be, in fact, the only pressure urging the burr against the atherosclerotic plaque. Under these conditions, a certain amount of damage to the healthy tissue is almost unavoidable, even though undesirable, and there is a clear risk of perforation. Thus, in clinical practice (balancing safety and residual stenosis), physicians rarely use a burr diameter of more than 2 mm, even on patients where the original diameter of the coronary artery lumen is estimated to be 3 mm. See, e.g., *Atherectomy, A Physicians Guide*, (Strategic Business Development, Inc., 1990), p. 96. These risks are enhanced at high rotational speeds where the differential cutting phenomenon is significantly diminished.

As indicated above, in clinical practice the opening of the stenosis of coronary (heart) arteries is performed very fast and thus very large numbers of small particles of stenotic material (estimated to be 1,000,000 per cubic mm of stenotic material removed—see id. at p. 92) are released into the coronary artery within a very short period of time. Although individually the particles (typically in the range of 5 microns) can easily pass through the capillaries, when such large numbers of such particles are released within a very short period of time it is very possible that there is a risk that they may at least temporarily occlude the capillaries. This may explain the heart pain which is not infrequently experienced by patients immediately after the Auth-type burr is passed across the stenosis, as well as elevated levels of enzymes indicative of myocardial ischemia (such as CPK) which have been documented in some patients after the Auth-type burr procedure. See id. at p. 95. There is yet a further disadvantage to the traditional rotating burr apparatus, particularly the device depicted in the '134 Auth patent. When such a device is used to open an arterial passageway which is quite narrow, the burr utilized must initially be relatively small. When the small-sized burr has been completely advanced through the stenosis, however, it cannot widen the passageway to a diameter larger than the diameter of the burr itself, and the burr must be exchanged for a larger diameter burr to continue the widening process. It is not unusual, and in fact is quite common, that at least two, and sometimes three or four progressively larger burrs are necessary to complete the task. Since the burrs are permanently attached to the flexible drive shaft, which in turn is permanently attached to the drive motor (or air turbine) and the associated proximal controls for the device, changing burr sizes means essentially exchanging the entire device (except for the guide wire) for a new one. Currently the cost of such devices is quite high, and the need to use multiple burr sizes multiplies this cost, making the procedure quite expensive.

It would therefore be advantageous to provide an abrasive burr based instrument which can provide directional control of removal of stenotic tissue allowing one to effectively remove eccentrically located stenotic material (e.g., atherosclerotic plaque) without any risk of damage (and thus risk of perforation) to normal vascular wall not covered with stenotic material. It would also be advantageous to provide such an instrument that would not completely occlude the blood flow through an artery during the atherectomy procedure, thus, not limiting the time available to the physician to open the stenosis. Furthermore, it would be advantageous to provide such an instrument that would allow slower, controlled release of particles of stenotic material into the capillaries over a longer period of time, thus reducing or eliminating the possibility of temporary cardiac ischemia (as evidenced by CPK elevation) and heart pain associated with passage of the burr across the stenosis. Also, it would be advantageous to provide a small diameter burr-based instrument capable of opening stenoses in large diameter peripheral arteries (such as the femoral and iliac arteries) without resorting to entry through a cut-down on the femoral artery. Finally, it would be extremely advantageous to provide such a device that can accomplish these objectives and also allow one to widely open stenotic vessels (e.g., atherosclerotic arteries) to their large original diameter without having to use multiple burrs of successively larger diameters, thus reducing the number of very expensive instruments needed for each procedure.

SUMMARY OF THE INVENTION

The invention relates to a directional rotational atherectomy device, and a method for its use, for removing tissues from body passageways, such as atherosclerotic plaques from arteries. The device utilized in the procedure includes an elongated catheter having at least first and second lumens and proximal and distal ends. The device includes a guide wire which can be advanced across the stenotic lesion in the passageway. The proximal end of the guide wire is received in the first lumen of the catheter so that the catheter can be advanced over the guide wire. A flexible, elongated drive shaft, having a central lumen, is disposed in the second lumen of the catheter and is longitudinally movable in this lumen of the catheter. An abrasive burr is carried at the distal end of the drive shaft, and the burr also includes a central lumen that is generally co-axial with the drive shaft lumen. A motor or air turbine is operatively connected to the proximal end of the drive shaft for rotating the drive shaft and burr at high speeds.

The lateral position of the burr within the body passageway is controlled by a positioning wire. The positioning wire is disposed in the drive shaft lumen, being inserted therein from the distal (burr) end of the drive shaft, and extends distally from the burr. The distal end of the positioning wire is slidably secured to the guide wire distally of the catheter and the burr so that the positioning wire can be moved proximally and distally with respect to the guide wire either together with or independently from the catheter.

The positioning wire further includes a distal burr-positioning segment that has a predetermined shape. The drive shaft and burr are movable longitudinally with respect to the positioning wire—thus, by advancing or retracting the drive shaft and burr with respect to the positioning wire, the burr can be selectively located along the burr-positioning segment of the positioning wire to selectively position the burr laterally of the guide wire. Positioning wires having distal burr-positioning segments with different shapes can be used to control both the lateral position and the angular orientation of the burr, providing great flexibility in positioning of the burr to remove unwanted tissue (such as an atherosclerotic plaque).

In a preferred embodiment, the positioning wire is made of a shape-memory alloy, such as nitinol. The fabrication of the positioning wire from such shape-memory alloy facilitates control of the lateral deflection of the burr—during insertion of the device into the body passageway over the guide wire, the catheter is advanced over a substantial portion (typically about the proximal half) of the burr-positioning segment of the positioning wire and substantially all of the length of the drive shaft, thereby straightening the distal burr-positioning segment of the positioning wire and bringing the burr to a lateral position close to the guide wire. In this configuration, the positioning wire is almost parallel to the guide wire, giving the distal end of the device a very low profile. Then, when the abrasive burr is located adjacent to the tissue to be removed, the catheter can be moved proximally with respect to the positioning wire and the drive shaft, thus freeing the burr-positioning segment of the positioning wire and allowing it to regain its predetermined shape, thereby moving the burr laterally away from the guide wire.

One of the significant advantages of the invention is that it allows intravascular ultrasonic imaging means to be used in conjunction with the device of the invention. Preferably the intravascular ultrasonic imaging means comprises a currently commercially available intravascular ultrasonic imaging catheter advanced over the guide wire to a position adjacent to the abrasive burr. To the extent that ultrasonic imaging guide wires become commercially available, they could easily be used in lieu of the conventional guide wire and intravascular ultrasonic imaging catheter. In either case, these devices allow intravascular ultrasonic imaging not only of a cross-section of the passageway (e.g., revealing the degree of stenosis in an artery) but also allow ultrasound imaging of the abrasive burr within the passageway relative to the stenosis (e.g., showing its position against an atherosclerotic lesion and showing the thickness of the lesion at that longitudinal location).

The method of removing tissue from a body passageway begins by selecting a directional rotational atherectomy device with an appropriate abrasive burr size (diameter) and an appropriate positioning wire. The proximal end of the positioning wire is then inserted into the distal end of the lumen of the drive shaft until it exits proximally from the housing (handle containing the turbine).

The guide wire is advanced into the body passageway until its distal end extends across the stenosis. Then the positioning wire (with the burr and flexible drive shaft, which is disposed in the second lumen of the catheter) and the catheter are advanced over the guide wire. Prior to advancing the positioning wire and catheter into the body passageway, the positioning wire and the drive shaft are withdrawn into the catheter until a significant portion (about the proximal one-half) of the positioning segment of the positioning wire and almost the entire length of the drive shaft become located within the catheter, thereby straightening the distal burr-positioning segment of the positioning wire and bringing the burr to a lateral position close to the guide wire. In this configuration, the positioning wire is almost parallel to the guide wire, giving the distal end of the device a very low profile. In such configuration, the positioning wire (with the burr and drive shaft) and the catheter are advanced over the guide wire until the positioning segment of the positioning wire and the burr are located longitudinally adjacent to the stenotic tissue to be removed. Then the catheter is slightly withdrawn proximally with respect to the positioning wire and the stenosis itself (i.e., positioning wire and burr with the drive shaft appear to be advanced with respect to the catheter) thus freeing the burr-positioning segment of the positioning wire and allowing it to at least partially regain its predetermined shape, thereby moving the burr laterally away from the guide wire.

The flexible drive shaft can similarly be advanced/retracted with respect to the positioning wire to selectively locate the burr along the burr-positioning segment of the positioning wire. Ordinarily, this will mean that the burr-positioning segment will cause the burr to be urged laterally against the stenotic tissue. The drive shaft and burr are then rotated at relatively high speed to abrade the tissue of interest. As the burr is rotated, it can also be moved distally and proximally (usually together with the positioning wire and the catheter) in the passageway, removing a portion of the tissue of interest (e.g., atherosclerotic plaque) as it is moved. The rotational position of the burr with respect to the guide wire and the stenotic tissue can be controlled by rotating the catheter in the body passageway.

The invention provides several distinct advantages over devices such as the Auth and Simpson atherectomy devices. With respect to Auth-type devices, there are a number of advantages to the present invention:

1. It provides directional control over the removal of stenotic tissue, reducing the risk of damage to or perforation of the normal vascular wall;

2. It allows one to widely open even large coronary arteries to their large original diameter without significant residual stenosis using a single directional rotational atherectomy instrument rather than multiple instruments with successively larger diameter burrs (which often still leave significant residual stenosis);

3. It provides a small diameter burr-based instrument capable of opening stenoses in large diameter peripheral arteries (such as the femoral and iliac arteries) without resorting to entry through a cut-down on the removal artery.

4. It permits use of intravascular ultrasound imaging to image a cross-section of the stenotic area (including the thickness and composition of the atherosclerotic plaque), and the relative position of the abrasive burr with respect to the stenotic tissue. The intravascular ultrasound imaging permits monitoring of the removal of the stenotic tissue as it is being removed, thus further enhancing the safety of the procedure;

5. It does not completely occlude the blood flow through an artery during an atherectomy procedure, thus not limiting the time available to the physician to open the stenosis; and 6. It provides for slower, controlled release of particles of stenotic material into the capillaries over a longer period of time. With respect to the Simpson-type atherectomy devices, the invention provides at least two additional advantages:

1. It is very flexible (compared to Simpson-type devices which typically have a rigid housing), permitting its use in small, more tortuous arteries; and 2. It is capable of removing hard, calcified stenotic tissue.

BRIEF DESCRIPTION OF THE DRAWINGS

FIG. 1 is a partially broken away view of the proximal and distal end portions of the directional rotational atherectomy device of the invention, shown somewhat schematically and in cross-section;

FIGS. 2-10 depict a sequence of steps in use of the directional rotational atherectomy device of the invention in removing a stenosis in an artery—

FIG. 2 is a partially broken away view of the directional rotational atherectomy device of the invention inserted into an artery having a stenosis to be removed, the burr-positioning segment of the positioning wire being located in the most narrow portion of the stenosis;

FIG. 3 is a partially broken away view similar to FIG. 2 showing the device with the catheter withdrawn proximally in relation to the stenosis and the positioning wire, the burr-positioning segment of the positioning wire having partially regained its predetermined shape, thus positioning the burr against the atherosclerotic plaque;

FIG. 4 is a view similar to FIGS. 2 and 3, with the burr having removed a portion of the atherosclerotic plaque;

FIG. 5 is a view similar to FIGS. 2-4 with the catheter, positioning wire, burr and drive shaft being withdrawn;

FIG. 6 is a view similar to FIG. 5, showing all components of the directional rotational atherectomy device except for the guide wire having been withdrawn;

FIG. 7 is a view similar to FIG. 2, with the directional rotational atherectomy device having been reinserted with a different positioning wire for continued removal of the stenosis;

FIG. 8 is a view similar to FIG. 3 but with an alternate positioning wire (with greater lateral deflection), its distal burr-positioning segment being freed from the catheter to urge the burr further laterally toward the stenosis;

FIG. 9 is a view similar to FIG. 8, showing continued removal of the stenosis;

FIG. 10 shows the directional rotational atherectomy device of the invention being withdrawn;

FIG. 11 is a view similar to FIG. 3 showing use of the directional rotational atherectomy device of the invention in removing a stenosis occurring at the ostium of a branch of an artery (an osteal stenotic lesion), the guide wire extending from the main artery into the branch artery;

FIG. 12 is a view similar to FIG. 11, showing an alternate position of the directional rotational atherectomy device in removing such an osteal stenotic lesion, the guide wire being located in the main artery only (i.e., not extending into the branch artery), and the positioning wire also having a distal burr-positioning segment with a different shape than the positioning wire shown in FIG. 11;

FIG. 13 is a partially broken away view of the proximal and distal end portions of the directional rotational atherectomy device of the invention, similar to FIG. 1, with the addition of an intravascular ultrasound imaging catheter positioned over the guide wire;

FIG. 14 depicts positioning of the directional rotational atherectomy device of the invention with such an intravascular ultrasound imaging catheter positioned within an artery adjacent to a stenotic segment of an artery;

FIG. 14A is a cross-sectional view of FIG. 14, taken along line 14A—14A thereof, and FIG. 14B represents the ultrasound image generated by the intravascular ultrasound imaging catheter at this position;

FIG. 15 is a view similar to FIG. 14, with the catheter and positioning wire rotated 90 degrees from the position shown in FIG. 14;

FIG. 15A is a cross-sectional view of FIG. 15, taken along line 15A—15A thereof, and FIG. 15B is an ultrasound image generated by the intravascular ultrasound imaging catheter at this position;

FIG. 16 illustrates a positioning wire having a radio-opaque marker (coating) on its distal burr-positioning segment;

FIG. 17 illustrates the directional rotational atherectomy device of the invention with a radio-opaque marker located near the distal end of the catheter;

FIGS. 18-24 illustrate several configurations of the positioning wire;

FIGS. 25-27 illustrate several possible configurations for the distal end of the positioning wire;

FIGS. 28-30 illustrate alternate embodiments for means connecting the distal end of the positioning wire slidably to the guide wire, and FIGS. 28A, 29A, and 30A are cross-sectional views, respectively, of FIGS. 28, 29, and 30;

FIG. 31 is a cross-sectional view of a guide wire having a stop located proximally to the distal end of the guide wire;

FIGS. 32-33 illustrate use of the directional rotational atherectomy device of the invention with the guide wire of FIG. 31, the advancement of the positioning wire against the stop causing lateral deflection of the burr;

FIG. 50 illustrates the use of braiding reinforcement in the catheter; and

FIG. 50A is a cross-sectional view of FIG. 50, taken along line 50A—50A.

BEST MODE FOR CARRYING OUT THE INVENTION

Figure 34:
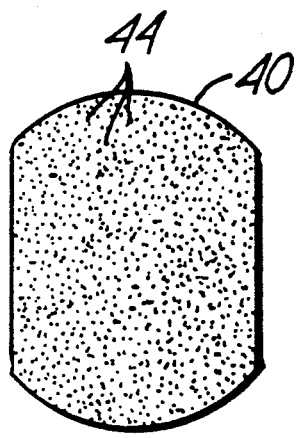
FIGS. 34-37 illustrate alternate embodiments for placement of diamond particles on the surface of the burr used in the invention.

Although the drawings illustrate use of the directional rotational atherectomy device of the invention in connection with removal of atherosclerotic plaques in arteries, the device is usable in other capacities, wherever tissue or obstructions are desired to be removed from a body passageways, cavities, or any organ or organ system of the body.

FIG. 1 illustrates the principal components of the device. An elongated catheter 20 includes at least a pair of lumens 24 and 26. The first of these is sized to receive a conventional guide wire 90 having an elongated shaft 96 and a conventional helically wound distal tip portion 94, terminating in a rounded tip 92.

In the other lumen 26 of the catheter 20, a multistrand helically wound flexible drive shaft 50 is disposed. The shaft 50 is generally comprised of a helical coil 52, at least the distal portion of which is preferably encased in a thin, flexible Teflon ® sheath 54. An abrasive burr 40 is carried at the distal end of the flexible drive shaft 50, and it includes a central lumen 46 generally coaxial of the central lumen 56 of the flexible drive shaft.

A positioning wire 70 is disposed in the lumen 56 of the flexible drive shaft 50. The positioning wire 70 includes a distal end 74 which is slidably secured about the shaft 96 of the guide wire 90, and a distal burr-positioning segment 72 which has a predetermined shape. The shape illustrated in FIG. 1 is such that the abrasive burr 40 is positioned laterally away from the guide wire 90.

The proximal portion of the catheter 20, as shown in the lower half of FIG. 1, is secured to a housing 34. Operatively attached to the housing 34 is a fitting 32 through which the guide wire shaft 96 can be advanced and withdrawn. A turbine 35 (or equivalent source for rotational motion) is secured to a turbine mount 37 slidably received in the housing 34. Relative longitudinal sliding movement of the turbine mount 37 with respect to the housing 34 is permitted, and, when it is desired to lock the longitudinal position of the turbine 35 and turbine mount 37 with respect to the housing 34, wing nuts 38 can be tightened on threaded bolts 39 (which extend from the turbine mount 37 through slots 36 in the housing 34). Alternately, equivalent means may be used to prevent relative longitudinal movement of the turbine and turbine mount with respect to the housing.

The turbine 35 is connected by way of turbine link 64 to the flexible drive shaft 50. A conventional seal 66 may be provided against the outer surface of the turbine link 64, preventing fluid from escaping from the cavity 65 while permitting rotational and longitudinal movement of the flexible drive shaft 50 and the turbine link 64. A side port 67 may be provided to permit infusion of lubricating fluid (saline or glucose solutions and the like) or radio-opaque contrast solutions into the cavity 65 and the second lumen 26 of the catheter 20. The side port 67 could also be connected to a vacuum source for aspiration of fluid through the catheter's second lumen 26.

Set screws 61 and 62 are provided to selectively permit or prevent relative longitudinal movement of the positioning wire 70 with respect to the turbine mount 37 and with respect to the housing 34. Thus, if the set screw 62 is loosened while the screw 61 is tightened against the positioning wire, the positioning wire 70 and the flexible drive shaft 50 (which is rigidly connected to the turbine 35 and hence to the turbine mount 37) can be advanced and retracted as a unit with respect to the catheter 20 and the housing 34. Alternately, loosening of set screw 61 and tightening of set screw 62 will permit relative longitudinal movement of the flexible drive shaft and the burr with respect to the positioning wire 70 allowing one to locate the burr at an appropriate place on the burr-positioning segment of the positioning wire 70. When both set screws 61 and 62 are loosened then obviously one can move the positioning wire longitudinally relative to both the catheter 20 and the flexible drive shaft and the burr.

Although the means for securing the positioning wire 70, the turbine mount 37, and the housing 34 with respect to one another are illustrated in the drawing as being accomplished by use of wing nuts 38 and set screws 61 and 62, it will be appreciated that other conventional means or mechanisms (such as cam friction fittings, and the like) may easily be employed. Moreover, the connection of the proximal end of the catheter 20 to the housing 34, as well as the side port 67 and guide wire fitting 32 are shown somewhat schematically—any of a variety of conventional fittings that are readily commercially available or adaptable for this purpose may easily be employed.

FIGS. 2-10 illustrate the operation and function of the directional rotational atherectomy device of the invention in removing an atherosclerotic lesion or atheroma 12 from an artery 10. As indicated above, the device of the invention is particularly useful in removing asymmetrical stenotic lesions, such as the one illustrated in FIGS. 2-10. Although the device will work just as well with symmetrical stenotic lesions or only mildly asymmetrical stenotic lesions, the advantages of the invention are best illustrated with respect to an atherosclerotic lesion that is located predominantly on one side of the arterial wall 10.

Commercially available angioplasty equipment (e.g., arterial puncture needles, arterial dilators, sheath introducers and guide catheters) and routine angioplasty techniques are used to appropriately position the directional rotational atherectomy device in the arteries of interest.

In FIG. 2, the guide wire 90 has been advanced through the artery to a position where its distal tip 92 is located distally of the stenosis. The catheter 20, including the positioning wire 70 and the burr 40 carried by the flexible drive shaft 50, has been advanced over the shaft 96 of the guide wire 90 to a position locating the burr 40 adjacent to the stenotic lesion 12. Note that during advancement of the catheter 20 through the artery, the catheter 20 has been advanced over a substantial portion (typically about the proximal one-half) of the distal burr-positioning segment 72 of the positioning wire 70 and almost all of the length of the distal portion of the flexible drive shaft. This temporarily straightens (not completely, but substantially) the distal burr-positioning segment 72 of the positioning wire 70 (which preferably is made of a shape-memory alloy such as nitinol), bringing the burr 40 to a lateral position close to the guide wire 90 with the positioning wire 70 almost parallel to the guide wire 90, and thereby giving the entire device a very low profile. Such a low profile of the distal end of the directional rotational atherectomy device will enable the device to be advanced even into an area of very tight arterial stenosis.

In FIG. 3, the catheter 20 has been withdrawn with respect to the distal burr-positioning segment 72 of the positioning wire 70, freeing the burr-positioning segment 72 from the confines of the catheter 20, and allowing it to at least partially regain its predetermined shape. Since the burr 40, being positioned on the distal burr-positioning segment 72, is engaged against the atherosclerotic lesion 12, the distal burr-positioning segment 72 has not entirely regained its predetermined shape in FIG. 3, being limited by the presence of the atherosclerotic plaque. In FIG. 3, the burr 40 has been positioned at the crown of the burr-positioning segment 72 of the positioning wire 70, putting the lateral surface of the burr 40 in direct contact with the atherosclerotic plaque 12.

At this point, the positioning wire 70, the catheter 20 and the flexible drive shaft 50 carrying the burr 40 can be advanced distally and retracted proximally as a unit while the burr is being rotated at relatively high speed (typically in the range of about 30,000 RPM to about 600,000 RPM, or even more, depending only on the physical dimensions and capabilities of the turbine/motor, flexible drive shaft and burr) to selectively remove a portion of the stenotic lesion 12.

In FIG. 4, a portion of the stenotic lesion 12 has been removed, and the distal burr-positioning segment 72 of the positioning wire 70 has now entirely regained its predetermined shape. Thus, at this point there is no significant further pressure of the burr 40 against the atherosclerotic lesion 12.

FIGS. 5-7 depict the successive removal of the directional rotational atherectomy device (except for the guide wire) and replacement of the positioning wire 70 with a different positioning wire 70' having a distal burr-positioning segment with a different shape which offers greater lateral deflection. Replacement of the positioning wire 70 can easily be accomplished by (1) withdrawing, if necessary, a substantial portion (typically the proximal half) of the burr-positioning segment of the positioning wire 70, along with the distal portion of the drive shaft, into the catheter 20, (2) withdrawing the positioning wire 70, together with the burr 40, its flexible drive shaft 50, and the catheter 20, out of the patient's body and further proximally off the proximal end of the guide wire 90, (3) removing the positioning wire 70 from the central lumen 56 of the flexible drive shaft 50 by pulling it distally therefrom, (4) inserting the new positioning wire 70' into the lumen 56 of the flexible drive shaft 50 by inserting the proximal end of the positioning wire 70' into the distal end of the drive shaft 50, (5) again advancing the catheter 20 over the proximal portion of the positioning segment of the positioning wire and almost the full length of the drive shaft to again bring the burr 40 to a lateral position close to the guide wire, so that the distal end of the device again assumes a very low profile to facilitate its introduction back into the artery, and (6) advancing the positioning wire 70', the burr 40 with its drive shaft 50 and catheter 20 as a unit over the guide wire 90 to the position illustrated in FIG. 7 with the burr 40 again positioned adjacent to the atherosclerotic lesion 12.

Once in this position, the catheter can again be withdrawn with respect to the positioning wire 70', thus allowing the distal burr-positioning segment 72' of the positioning wire 70' to again at least partially regain its predetermined shape, as illustrated in FIG. 8, thereby moving the burr laterally away from the guide wire and up against the atherosclerotic lesion 12. More of the atherosclerotic lesion 12 can then be removed, as illustrated in FIG. 9, until the distal burr-positioning segment 72' has again fully regained its predetermined shape. When a sufficient amount of the lesion 12 has been removed, if necessary, the burr-positioning segment 72' can again be withdrawn into the catheter 20 (or, equivalently, the catheter advanced over the burr-positioning segment) to again draw the burr close to the guide wire 90, and the entire device, including the guide wire, can be withdrawn, as shown in FIG. 10.

As can be seen from the above discussion in reference to the drawings, during the entire procedure the abrasive burr 40 never need come into contact with the wall 10 of the artery across from the atherosclerotic lesion 12. Rather, the invention provides directional control over the lateral location of the burr within the artery, permitting contact of the burr substantially only with stenotic tissue. Concerns about damage to healthy tissue (including concerns about perforation) are thus substantially reduced.

Moreover, lumens of a very large arteries can be re-opened to their original diameter (e.g., 5-7 mm in the iliac and femoral arteries) with use of a comparatively small abrasive burr (e.g., 2 mm in diameter), a capability not preactically possible with the Auth-type device, which usually requires performing a cut-down on the common femoral artery in order to introduce the larger burrs (e.g., over 3 or 4 mm in diameter) of the Auth-type device. In some cases this would be entirely impossible, as the normal diameter of the artery through which the burr preferably is introduced may only be, e.g., 3-4 mm or less. An example of this would be using the brachial artery approach (having a diameter of about 3-4 mm or less) to reach the iliac or femoral artery (having a diameter of 5-7 mm).

FIGS. 11 and 12 illustrate additional flexibility that the invention provides in gaining access to treat atherosclerotic lesions occurring at otherwise difficult treatment locations. Both FIGS. 11 and 12 depict an osteal stenotic lesion (i.e., a lesion occurring in the area of the origin of a branch in an artery). In FIG. 11, the guide wire 90 is advanced through the primary artery 14 into the branch artery 15. A positioning wire 70 is then selected having a mild curvature of the distal burr-positioning segment 72. Removal of the stenotic material 12 can thus be accomplished without contact of the abrasive burr 40 with the wedge-shaped junction 16 in the artery. In contrast, conventional burr atherectomy devices such as that described in the Auth patent identified above would place significant pressure on the wedge-shaped junction 16 in order to properly position and urge the burr against stenotic material in the branch artery 15.

In FIG. 12, an alternate position of the device of the invention is shown. In this embodiment, the guide wire 90 remains in the main artery, and the positioning wire 70 includes a distal burr-positioning segment 72 having a more sharply arcuate form, permitting engagement of the abrasive burr 40 against the atheroma 12 without placing any pressure with the rotating abrasive burr on the wedge-shaped junction 16.

The directional rotational atherectomy device of the invention is particularly well suited for use with intravascular ultrasound imaging technology. As illustrated in FIG. 13, an intravascular ultrasound imaging catheter 100 may be advanced over the guide wire 90 through the first lumen 24 of the catheter 20. Ultrasound transducer elements 102 (indicated schematically) can then be positioned adjacent to the abrasive burr 40 in the same cross-sectional plane of the passageway, permitting imaging of the thickness and composition of the atherosclerotic plaque, the relative position of the abrasive burr with respect to the stenotic tissue, and imaging of removal of the stenotic tissue as it is being removed.

FIGS. 14 and 15 illustrate both the utility of this imaging technique and the rotational directional control of the entire device within an artery. FIG. 14A shows in cross section an artery with an atherosclerotic lesion 12 partially obstructing blood flow in an artery 10. The directional rotational atherectomy device of the invention has been advanced into location for removal of the lesion 12. The ultrasound imaging elements 102 of the intravascular ultrasound imaging catheter 100 have been positioned in the same cross-sectional plane of the artery as the burr 40. In FIG. 14A, the catheter 20 has been positioned rotationally in the artery so that the intravascular ultrasound imaging catheter 100 is lying laterally to the left of the burr 40 (appearing to lie behind the burr and its flexible drive shaft in FIG. 14). In FIGS. 15 and 15A, the catheter 20 has been rotated 90 degrees to move the burr 40 to a different rotational position within the artery, this time appearing in both FIGS. 15 and 15A to be located directly above the ultrasound imaging catheter 100. Thus, one can not only selectively position the burr 40 laterally with respect to the guide wire 90 (by selecting the appropriate positioning wire 70) but can also control the rotational position of the burr 40 within the artery by rotation of the catheter 20 and the positioning wire 70.

FIGS. 14B and 15B illustrate the expected ultrasound image generated by the intravascular ultrasound imaging catheter 100. The abrasive burr 40 provides an echo 40' and casts a shadow 42 which clearly locate the burr's position with respect to the stenosis 12 and to the intravascular ultrasound imaging catheter 100. The depth of the atherosclerotic lesion 12 is also visible. Viewing the ultrasound image, therefore, permits accurate rotational positioning of the abrasive burr 40 within the artery to selectively position the abrasive burr 40 only against tissue desired to be removed and to monitor the progress of stenotic lesion removal throughout the procedure.

As described above, preferably the intravascular ultrasound imaging device comprises a commercially available intravascular ultrasound imaging catheter advanced over the guide wire to a position adjacent to the abrasive burr. Such intravascular ultrasound catheters are available, e.g., from Cardiovascular Imaging Systems, Inc. (Sunnyvale, Calif.), Boston Scientific Corp. (Watertown, Mass.), and Endosonics, Inc. (Pleasanton, Calif.). To the extent that ultrasonic imaging guide wires become commercially available, they could easily be used in lieu of the conventional guide wire and intravascular ultrasound imaging catheter depicted in the drawings.

Figures 16, 17:
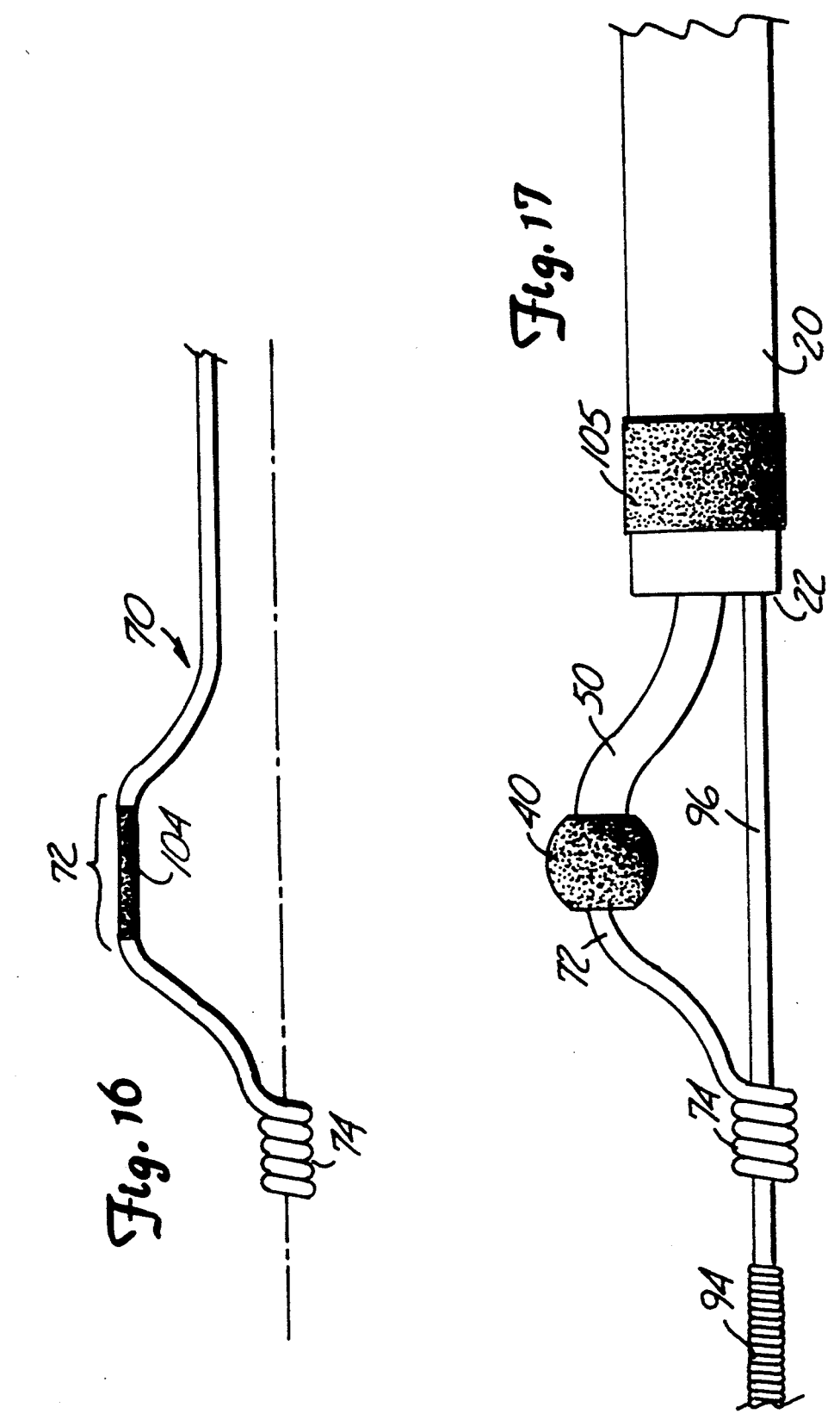

Conventional fluoroscopic imaging techniques (with or without radio-opaque contrast solution injections) should also be utilized in performing the directional rotational atherectomy procedure. The longitudinal and rotational positioning of the device within the artery may be assisted by placing special radio-opaque markings on the elements of the device. For this purpose, as illustrated in FIG. 16 and 17, conventional radio-opaque markings 104 and 105 can be placed respectively on the positioning wire 70 and the catheter 20 (see FIG. 16 and 17). On a positioning wire, such markings may simply comprise a thin layer of gold, platinum or similar radio-opaque material. Similar conventional markings (such as gold or platinum rings) can be placed on other components, and/or components can themselves be manufactured from radio-opaque materials.

FIGS. 18-24 depict a variety of possible shapes for the distal burr-positioning segment 72 of the positioning wire 70. These burr-positioning segments are respectively identified as 72a, 72b, 72c, 72d, 72e, 72f, and 72g. The shapes shown in FIGS. 23 and 24 are essentially similar to one another except that the positioning segment in FIG. 24 will displace the abrasive burr further laterally away from the guide wire than the positioning segment shown in FIG. 23. FIGS. 18-22 provide shapes giving a variety of angular orientations within the artery—i.e., it is possible using such shapes to orient the abrasive burr 40 along an axis that is not parallel to the axis of the guide wire 90. This provides great flexibility for selectively removing stenotic tissue (such as is illustrated in FIGS. 11-12).

FIGS. 25-27 illustrate three possibilities for forming the distal end 74 of the positioning wire. FIG. 25 illustrates in cross-section a simple helical coil formed by the distal portion of the positioning wire 70. The windings of the helical coil together define a central cylindrical opening sized to receive the shaft 96 of the guide wire 90 therein. In FIG. 26, the outer surface of the coiled distal portion 74 has been machined so as to taper it distally inwardly. Such a configuration presents a lower profile while being advanced through the artery. FIG. 27 illustrates another embodiment where both the outer surface and the inner surface of the coil have been machined to present generally flat inner and outer surfaces.

FIGS. 28-30 present alternate embodiments for slidably securing the distal end of the positioning wire 70 to the guide wire 90. A guide 76 is secured to the distal end of the positioning wire 70, the guide 76 including a guiding lumen 77 in which the shaft 96 of the guide wire may be slidably disposed. FIGS. 29 and 29A illustrate one embodiment of such a guide 76' in which the upper portion, through which the distal end of the positioning wire 70 is disposed and secured, has an intermediate void portion leaving part of the positioning wire 70 exposed—in some circumstances, this configuration may be easier to manufacture than the more solid configuration illustrated in FIGS. 28 and 28A. Alternately, as shown in FIGS. 30 and 30A, the guide 76" may have a generally "H"-shaped cross-sectional profile, the upper portion of which is securely attached to the distal end of the positioning wire 70, and the lower portion of which is slidably received over the guide wire shaft 96. Other suitable configurations may also be utilized.

The guide wire 90, the positioning wire 70, and the guide 76 all can be provided with a slippery surface coating such as TEFLON ®, silicone, a combination of silicone over TEFLON ®, or similar slippery material. A particularly slippery surface can be obtained by utilizing PHOTOLINK ® brand surface modification commercially available from Bio-Metric Systems, Inc. of Eden Prairie, Minn.

FIGS. 31-33 illustrate an alternate embodiment of the invention in which a stop 98 is securely attached near the distal end of the guide wire shaft 96. The positioning wire 70 can be advanced until the distal end portion 74 of the positioning wire 70 engages the stop 98; at this point, further advancement of the positioning wire 70 will cause the distal burr-positioning segment 72 of the positioning wire 70 to flex laterally outwardly, thereby increasing the distance between the abrasive burr 40 and the guide wire shaft 96. This configuration provides greater flexibility for controlling the lateral position of the abrasive burr within the artery without having to exchange positioning wires 70.

Figure 35:
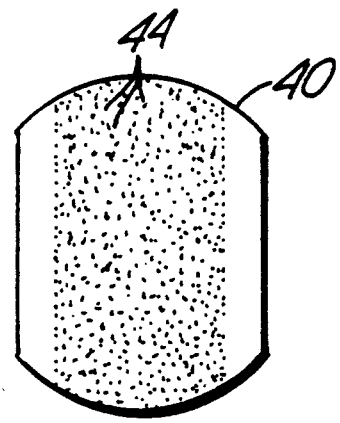
Figure 36:
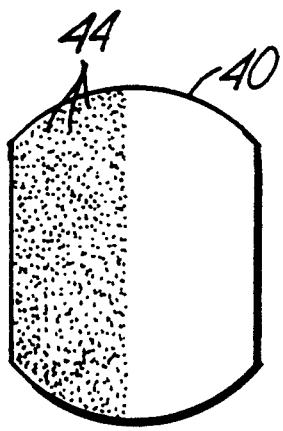
Figure 37:
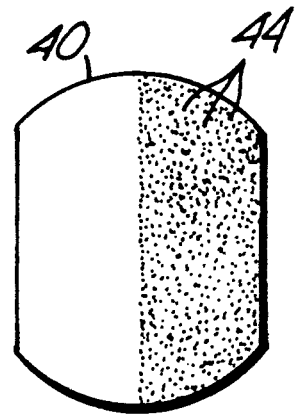

Preferably the shape of the burr is generally frustospherical, i.e., the abrading portion of the burr is generally spherical. Other shapes can also be used, including, e.g., ellipsoidal shapes. The body of the burr can be made from various materials including metals, ceramics and the like. Preferably it is made from stainless steel and is coated with a suitable abrasive material, such as diamond powder, fused silica, titanium nitride, tungsten carbide, aluminum oxide, boron carbide, or other ceramic materials. Although the abrasive coating on the burr of the invention may utilize any of the abrasive materials mentioned above, prefer-ably it is comprised of diamond chips (or diamond dust particles) attached to the surface of a suitable substrate, using well known techniques, such as conventional electroplating or fusion technologies (see, e.g., U.S. Pat. No. 4,018,576). Buffs of this type have been used in a variety of medical/dental applications for years and are commercially available from companies such as Abrasive Technologies, Inc. of Westerville, Ohio. FIGS. 34-37 illustrate several possible configurations for distribution of diamond particles 44 on the abrasive burr 40. In FIG. 34, the diamond particles 44 are fairly uniformly distributed across the surface of the burr 40. In FIG. 35, the particles extend only along a central band about the burr 40. FIGS. 36 and 37 respectively illustrate distribution of the diamond particles on the forward and backward portions of the burr. Any suitable distributions of such particles can be utilized to achieve the desired functionality of the burr.

Figure 38:
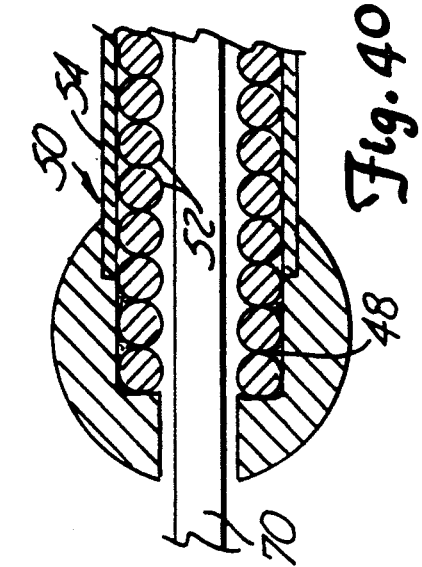
FIGS. 38-43 illustrate several embodiments for attaching the burr to the distal end of the flexible drive shaft.
Figure 39:
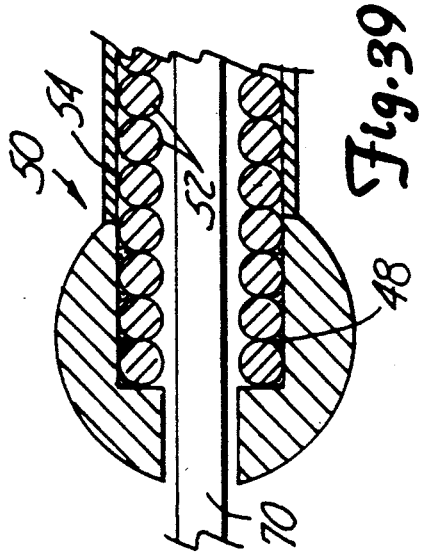
Figure 40:
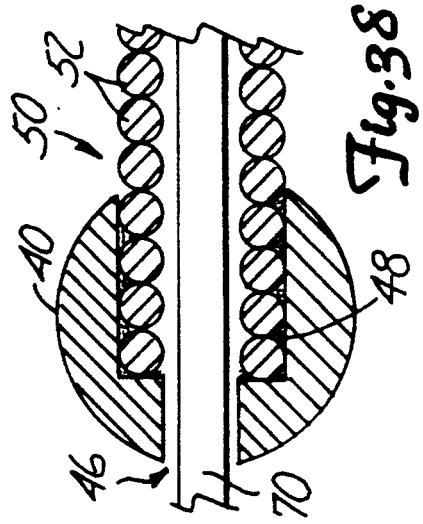

FIGS. 38-43 depict several alternate embodiments for attachment of the burr 40 to the multistrand (typically two or three strands) helically wound flexible drive shaft 50. FIG. 38 shows a burr having a central lumen 46 which has a diameter that is larger on the proximal end than on the distal end. In this embodiment, the drive shaft 50 does not extend all the way through the burr, giving a somewhat larger outer surface area on the distal portion of the burr onto which abrasive particles (typically diamond particles) can be attached. FIG. 39 shows the addition of a thin outer sheath 54 for presenting a smooth, low friction surface on the drive shaft 50. The sheath 54 preferably is made of a material such as TEFLON ®, or similar slippery material. FIG. 40 shows a further modification where the distal end of the sheath 54 is countersunk into the burr.

Figure 41:
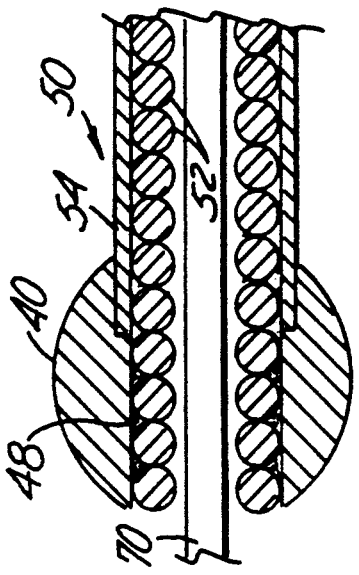
Figure 42:
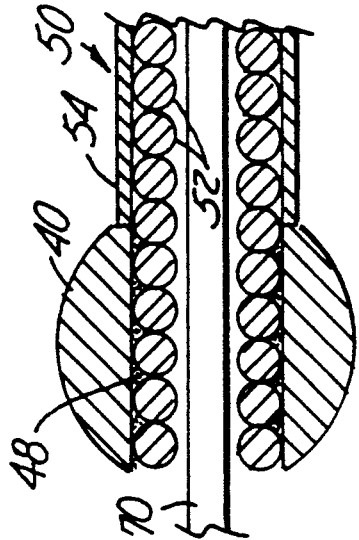
Figure 43:
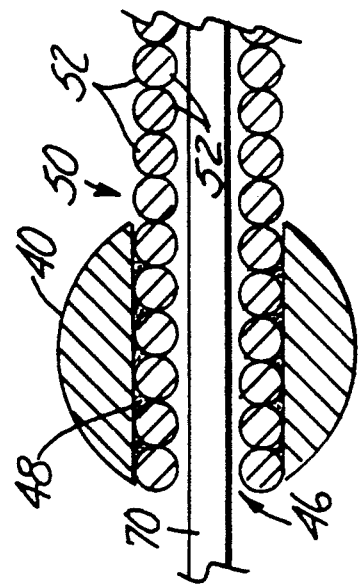

FIG. 41 shows a slightly different embodiment for the burr where the central lumen 46 of the burr is of uniform diameter, and the coil of the drive shaft extends entirely through the burr. FIGS. 42 and 43 correspond to FIGS. 39 and 40, by adding the outer, low friction sheath 54, with such sheath 54 being countersunk into the burr in FIG. 43.

Figure 45:
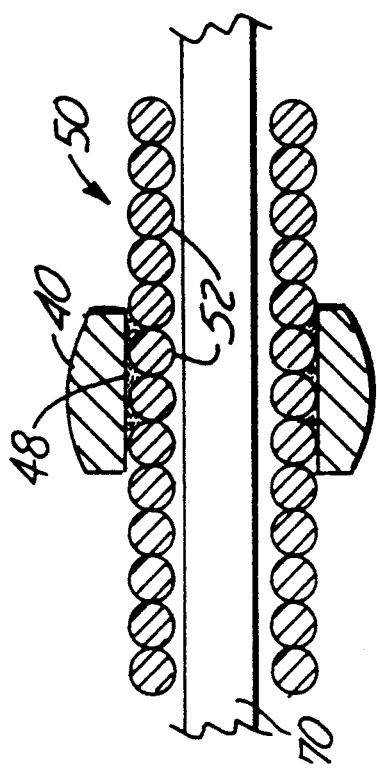
FIGS. 44-47 illustrate several embodiments for attaching a burr to a section of the drive shaft located proximal to the distal end of the drive shaft.
Figure 47:
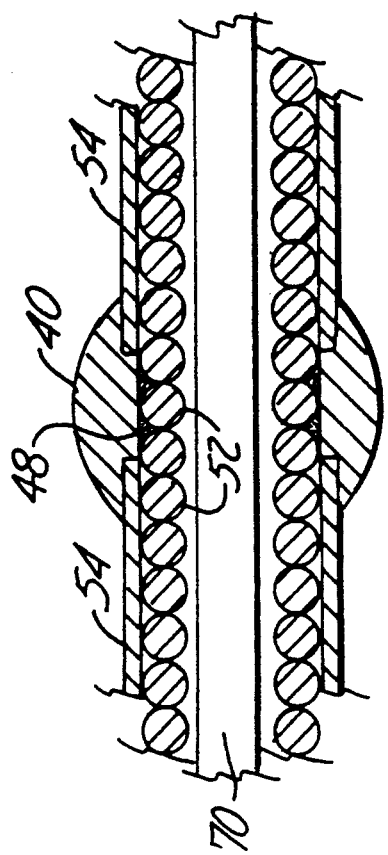
Figure 44:
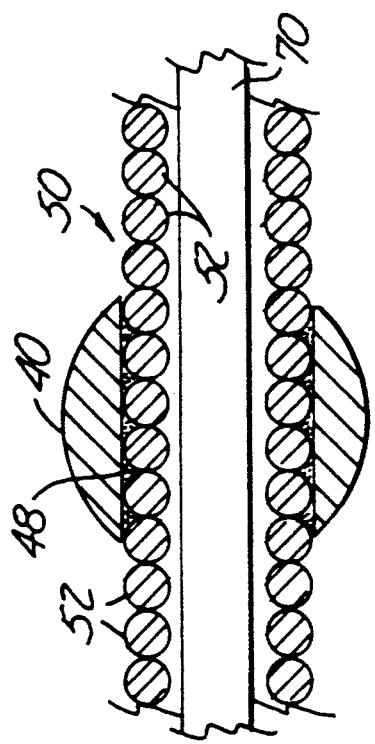
Figure 46:
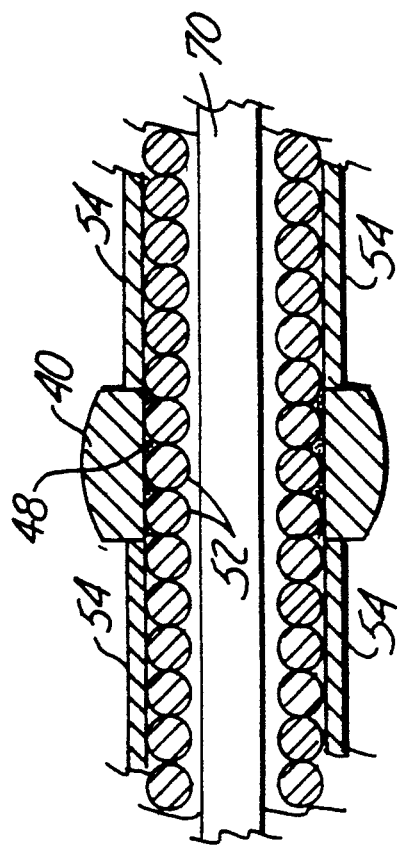

FIGS. 44-47 depict further embodiments in which the flexible drive shaft 50 continues distally beyond the burr. FIGS. 44 and 45 are presented without an outer sheath and FIGS. 46 and 47 depict an outer sheath 54 over the flexible drive shaft 50.

The burr 40 can be attached to the drive shaft 50 by any suitable means, including brazing, adhesives, and the like. In the drawings, the burr 40, is depicted as attached to the drive shaft by an adhesive 48. Suitable adhesives include epoxy resins, cyanoacrylates, and the like.

Figure 48:
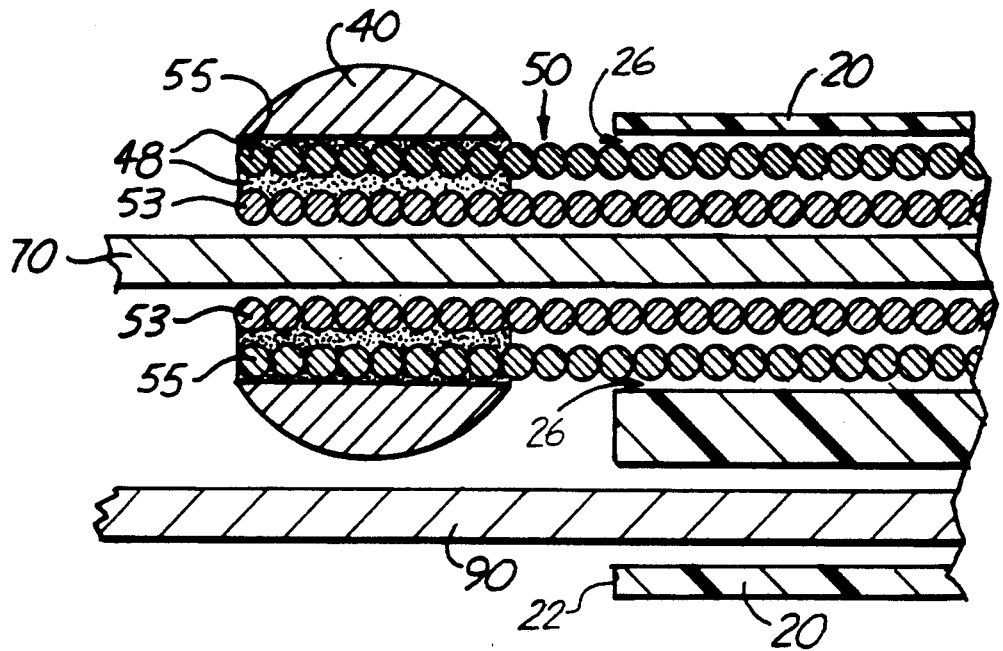
FIGS. 48-49 illustrate the use of a two-layer helically wound flexible drive shaft.
Figure 49:
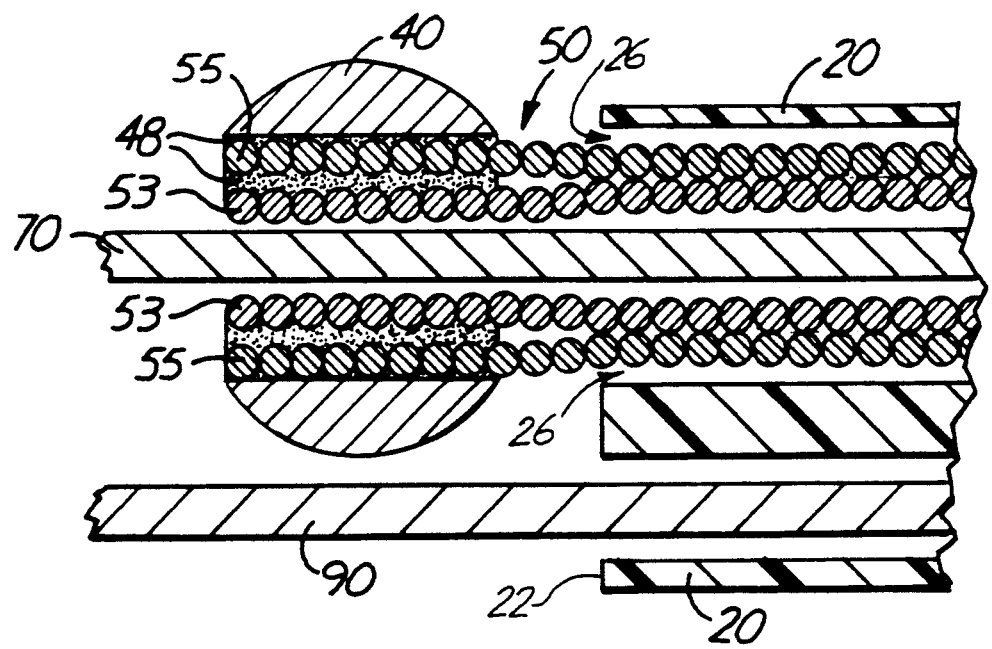

FIGS. 48 and 49 depict the use of a two-layer helically wound flexible drive shaft. In this embodiment, a pair of multi-strand coils 53 and 55 is disposed co-axially—one of them is wound counterclockwise, and the other is wound clockwise. Thus, viewing the burr from its distal end, when the burr is rotated in the direction of the winding of the outer coil 55, torque on that coil will tend to decrease its diameter, while torque on the inner coil 53 will tend to increase its diameter. Thus, the opposing forces of the two coils against one another, as depicted in FIG. 49, will result in there being a slight increase in the gap between the inner wall of the catheter lumen 26 and the outer coil 55, as well as a slight increase in the gap between the outer surface of the positioning wire 70 and the inner surface of the inner coil 53. This will not only diminish the friction of the flexible drive shaft against the catheter lumen and the positioning wire, but will also decrease the risk of the flexible drive shaft either unwinding in the artery or locking onto the positioning wire. For applications in very small arteries, it may not be practical to use a two layer flexible drive shaft because of the inherent increase in diameter caused by the second layer.

The single layer multistrand helically wound flexible coil 52 and the two-layer flexible drive shaft described above are preferably made from stainless steel wire. Coils of this type are generally commercially available.

The catheter 20 can be made from conventional catheter materials, including flexible thermoplastic or silicone materials. For example, the catheter preferably is made from a slippery material such as TEFLON ®, and can be reinforced with an outer layer made of nylon or other similar materials having desirable torque transmitting characteristics. FIG. 50 illustrates a catheter 20 that includes mesh reinforcement 28 (thin wire braiding) along substantially its entire length to improve the torque response of the catheter, reducing the likelihood of "whip" or "ratcheting" of the catheter as it is rotated in the artery to selectively locate the burr against the stenosis. FIG. 50A is a cross-sectional view illustrating that third and fourth lumens 29 and 30 can be provided for delivery or suction of fluids through the catheter (such as saline, radio-opaque contrast solutions, blood and the like).

While a preferred embodiment of the present invention has been described, it should be understood that various changes, adaptations and modifications may be made therein without departing from the spirit of the invention and the scope of the appended claims.

What is claimed is:

1. A directional rotational atherectomy device, comprising:

an elongated catheter having at least first and second lumens, and a distal end;

a guide wire receivable in the first lumen of the catheter and extending distally therefrom;

a flexible, elongated drive shaft having proximal and distal ends and a central lumen, the drive shaft being receivable in the second lumen of the catheter and being longitudinally movable therein;

means operatively connected to the proximal end of the drive shaft for rotating the drive shaft;

an abrasive burr carried by the drive shaft, the burr including a central lumen generally coaxial with the drive shaft lumen; and a positioning wire receivable in the drive shaft lumen, the positioning wire having a distal end and means for slidably securing the distal end of the positioning wire about the guide wire distally of the distal end of the catheter so that the positioning wire can be moved proximal and distally with respect to the guide wire, the positioning wire further including a distal burr-positioning segment having a predetermined shape, the drive shaft and burr being movable longitudinally with respect to the positioning wire and the catheter to selectively locate the burr along the predetermined shape of such distal burr-positioning segment;

at least the proximal portion of the burr-positioning segment of the positioning wire being retractable into and advanceable out of the catheter, the predetermined shape of the distal burr-positioning segment of the positioning wire being curved so that when the burr is positioned along such curve and such proximal portion of the burr-positioning segment is retracted into the catheter, the burr will be drawn to a position close to the guide wire, and when the proximal portion of the curved burr-positioning segment of the positioning wire is advanced out of the catheter the predetermined curved shape of the distal burr-positioning segment spaces the burr laterally further away from the guide wire, 2. The directional rotational atherectomy device of claim 1 wherein the means for slidably securing the distal end of the positioning wire to the guide wire comprises a generally cylindrical sleeve received closely about the guide wire.

3. The directional rotational atherectomy device of claim 2 wherein the sleeve comprises a generally cylindrical bushing attached to the distal end of the positioning wire.

4. The directional rotational atherectomy device of claim 2 wherein the sleeve comprises a helical winding of the distal end portion of the positioning wire.

5. The directional rotational atherectomy device of claim 1 wherein the positioning wire is made of a shape-memory alloy.

6. The directional rotational atherectomy device of claim 5 wherein the alloy is nitinol.

7. The directional rotational atherectomy device of claim 1 further comprising a stop positioned on the guide wire distally of the distal end of the positioning wire and against which the distal end of the positioning wire can engage so that further advancement of the positioning wire will cause the burr-positioning segment to flex laterally away from the guide wire, thereby changing the lateral position of the burr when it is located over the distal burr-positioning segment.

8. The directional rotational atherectomy device of claim 1 wherein the positioning wire is movable longitudinally to selectively advance and retract the burr-positioning segment of the positioning wire between a first position, where it is substantially confined in the second lumen of the catheter to a generally straight configuration, and a second position where it is advanced distally out of the catheter's second lumen.

9. The directional rotational atherectomy device of claim 1 further comprising intravascular ultrasound imaging catheter means advancable over the guide wire to a position adjacent the abrasive burr for providing a cross-sectional image of tissue of interest and of the position of the abrasive burr with respect to such tissue.

10. The directional rotational atherectomy device of claim 9 including means for securing the intravascular ultrasound imaging catheter with respect to the drive shaft carrying the burr so that the intravascular ultrasound imaging catheter and drive shaft can be advanced and retracted as a unit with respect to the tissue of interest.

11. The directional rotational atherectomy device of claim 1 wherein the guide wire includes intravascular ultrasonic imaging means for providing a cross-sectional image of tissue of interest and of the position of the abrasive burr with respect to such tissue.

12. The directional rotational atherectomy device of claim 1 wherein the guide wire is made of a shape-memory alloy.

13. The directional rotational atherectomy device of claim 12 wherein the alloy is nitinol.

14. The directional rotational atherectomy device of claim 1 wherein the flexible, elongated drive shaft is comprised of a multi-strand helical coil.

15. The directional rotational atherectomy device of claim 1 wherein the drive shaft is comprised of a pair of multi-strand helical coils disposed co-axially of one another.

16. The directional rotational atherectomy device of claim 15 wherein one of the coils is wound clockwise and the other is wound counter-clockwise.

17. The directional rotational atherectomy device of claim 1 wherein the abrasive burr is generally spherical in shape.

18. The directional rotational atherectomy device of claim 1 wherein the abrasive burr comprises a body having an outer surface, and an abrasive material attached to such outer surface.

19. The directional rotational atherectomy device of claim 18 wherein the abrasive material is substantially evenly distributed over the outer surface of the body of the burr.

20. The directional rotational atherectomy device of claim 18 wherein the abrasive material is substantially evenly distributed over a central portion of the outer surface of the body of the burr.

21. The directional rotational atherectomy device of claim 18 wherein the abrasive material is substantially evenly distributed over a distal portion of the outer surface of the body of the burr.

22. The directional rotational atherectomy device of claim 18 wherein the abrasive material is substantially evenly distributed over a proximal portion of the outer surface of the body of the burr.

23. The directional rotational atherectomy device of claim 18 wherein the abrasive material is diamond particles.

24. A directional rotational atherectomy device, comprising:
an elongated catheter having a distal end and at least first and second lumens with longitudinal axes;
a guide wire receivable in the first lumen of the catheter and extending distally therefrom;
a flexible, elongated drive shaft having proximal and distal ends and a central lumen, the drive shaft being receivable in the second lumen of the catheter and being longitudinally movable therein;
means operatively connected to the proximal end of the drive shaft for rotating the drive shaft;
an abrasive burr carried by the drive shaft, the burr including a central lumen having a central axis generally coaxial with the drive shaft lumen; and
a shape-memory alloy positioning wire receivable in the drive shaft lumen, the positioning wire having a distal end and means for slidably securing the distal end of the positioning wire about the guide wire distally of the distal end of the catheter so that the positioning wire can be moved proximally and distally with respect to the guide wire;
the positioning wire further including a distal burr-positioning segment having a predetermined curved shape, the drive shaft and burr being movable longitudinally with respect to the positioning wire and the catheter so that when the burr is positioned along such curved segment and such curved segment is positioned substantially entirely distally of the distal end of the catheter, the longitudinal axis of the burr is spaced laterally from the longitudinal axis of the second catheter lumen;
at least the proximal portion of the curved burr-positioning segment of the positioning wire being retractable into the catheter so that when the burr is positioned along such curve and the proximal portion of the burr-positioning segment is retracted into the catheter, the burr will be drawn to a position close to the guide wire;

the directional rotational atherectomy device further including intravascular ultrasound imaging catheter means advancable over the guide wire to a position adjacent the abrasive burr for providing a cross-sectional image of tissue of interest and of the position of the abrasive burr with respect to such tissue.

25. A method of removing tissue from a body passageway comprising the steps of:

(a) providing a directional rotational atherectomy device comprising:

a catheter having at least two lumens;

a guide wire which is receivable in a first of the catheter lumens;

a flexible, elongated drive shaft disposed in the other catheter lumen, the drive shaft having a central lumen and an abrasive burr carried on the drive shaft, the burr including a central lumen generally coaxial with the drive shaft lumen; and a positioning wire disposed in the drive shaft lumen and extending distally therefrom, the positioning wire including a distal end and means for slidably securing such distal end to the guide wire, the positioning wire further including a distal burr-positioning segment having a predetermined shape;

(b) advancing the guide wire into the body passageway and positioning the distal end of the guide wire distally of the tissue to be removed;

(c) advancing the positioning wire, the burr with its flexible drive shaft, and the catheter along the guide wire, with at least the proximal portion of the distal burr-positioning segment of the positioning wire being positioned in the catheter, until the burr is positioned adjacent to the tissue to be removed;

(d) withdrawing the catheter with respect to the burr-positioning segment of the positioning wire to allow such segment to at least partially regain its predetermined shape;

(e) moving the drive shaft, if necessary, to position the burr at the desired location along the burr-positioning segment of the positioning wire to selectively position the burr laterally of the guide wire within the body passageway; and (f) rotating the drive shaft and burr to remove the tissue.

26. The method of claim 25 further comprising the step of withdrawing the positioning wire, the burr with its drive shaft, and the catheter from the body passageway, replacing the positioning wire with a second positioning wire having a distal burr-positioning segment with a predetermined shape which is different from the predetermined shape of the first positioning wire, and reinserting the second positioning wire, the burr with its drive shaft, and the catheter to a position locating the burr adjacent the tissue to be removed.

27. The method of claim 25 including the steps of advancing an intravascular ultrasound imaging catheter over the guide wire to a position adjacent to the tissue to be removed from the body passageway, and utilizing the intravascular ultrasound imaging catheter to image a cross-section of the passageway.

28. The method of claim 25 wherein the imaging step includes positioning the ultrasound imaging catheter adjacent to the abrasive burr and imaging both the tissue to be removed and the relative position of the abrasive burr with respect to such tissue.

29. A directional rotational atherectomy device, comprising:

an elongated catheter having at least first and second lumens and a distal end;

a guide wire receivable in the first lumen of the catheter and extending distally therefrom;

a flexible, elongated drive shaft having proximal end and distal ends and a central lumen, the drive shaft being receivable in the second lumen of the catheter and being longitudinally movable therein;

means operatively connected to the proximal end of the drive shaft for rotating the drive shaft;

an abrasive burr carried by the drive shaft, the burr including a central lumen generally coaxial with the drive shaft lumen; and a positioning wire receivable in the drive shaft lumen, the positioning wire having a distal end and means for slidably securing the distal end of the positioning wire about the guide with distally of the distal end of the catheter so that the positioning wire can be moved proximally and distally with respect to the guide wire, the positioning wire further including a distal burr-positioning segment having a predetermined shape, the drive shaft and burr being movable longitudinally with respect to the positioning wire and the catheter to selectively locate the burr along the predetermined shape of such distal burr-positioning segment to selectively position the burr laterally of the guide wire;

intravascular ultrasound imaging catheter means advanceable over the guide wire to a position adjacent the abrasive burr for providing a cross-sectional image of tissue of interest and of the position of the abrasive burr with respect to such tissue.

30. A directional rotational atherectomy device, comprising:

an elongated catheter having at least first and second lumens and a distal end;

a guide wire receivable in the first lumen of the catheter and extending distally therefrom;

a flexible, elongated drive shaft having proximal and distal ends and a central lumen, the drive shaft being receivable in the second lumen of the catheter and being longitudinally movable therein;

means operatively connected to the proximal end of the drive shaft for rotating the drive shaft;

an abrasive burr carried by the drive shaft, the burr including a central lumen generally coaxial with the drive shaft lumen; and a positioning wire receivable in the drive shaft lumen, the positioning wire having a distal end and means for slidably securing the distal end of the positioning wire about the guide wire distally of the distal end of the catheter so that the positioning wire can be moved proximally and distally with respect to the guide wire, the positioning wire further including a distal burr-positioning segment having a predetermined shape, the drive shaft and burr being movable longitudinally with respect to the positioning wire and the catheter to selectively locate the burr along the predetermined shape of such distal burr-positioning segment to selectively position the burr laterally of the guide wire;

the guide wire including intravascular ultrasonic imaging means for providing a cross-sectional image of tissue of interest and of the position of the abrasive burr with respect to such tissue.

31. A directional rotational atherectomy device, comprising:

an elongated catheter having a distal end and at least first and second lumens, such lumens each having a longitudinal axis;

a guide wire receivable in the first lumen of the catheter and extending distally therefrom;

a flexible, elongated drive shaft having proximal and distal ends and a central lumen, the drive shaft being receivable in the second lumen of the catheter and being longitudinally movable therein;

means operatively connected to the proximal end of the drive shaft for rotating the drive shaft;

an abrasive burr carried by the drive shaft, the burr including a central lumen and a longitudinal axis generally coaxial with the drive shaft lumen; and a positioning wire receivable in the drive shaft lumen, the positioning wire having a distal end and means for slidably securing the distal end of the positioning wire about the guide wire distal end of the catheter so that the positioning wire can be moved proximally and distally with respect to the guide wire, the positioning wire further including a distal burr-positioning segment having a predetermined shape, the drive shaft and burr being movable longitudinally with respect to the positioning wire and the catheter to selectively locate the burr along the predetermined shape of such distal burr-positioning segment, the predetermined shape of the distal burr-positioning segment of the positioning wire being curved so that when the burr is positioned along such curve and such curve is positioned substantially entirely distally of the distal end of the catheter, the longitudinal axis of the burr is spaced laterally from the longitudinal axis of the second catheter lumen.

32. The directional rotational atherectomy device of claim 31 wherein at least the proximal portion of the curved burr-positioning segment of the positioning wire is retractable into the catheter so that when the burr is positioned along such curve and such proximal portion of the burr-positioning segment is retracted into the catheter, the burr will be drawn to a position close to the guide wire.

* * * * *